(12) United States Patent
Nakayama

(10) Patent No.: US 11,109,811 B2
(45) Date of Patent: Sep. 7, 2021

(54) WAVEFORM ESTIMATION APPARATUS, WAVEFORM ESTIMATION METHOD, AND NON-TRANSITORY COMPUTER-READABLE STORAGE MEDIUM

(71) Applicant: FUJITSU LIMITED, Kawasaki (JP)

(72) Inventor: Osafumi Nakayama, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 171 days.

(21) Appl. No.: 16/194,426

(22) Filed: Nov. 19, 2018

(65) Prior Publication Data
US 2019/0150847 A1 May 23, 2019

(30) Foreign Application Priority Data

Nov. 20, 2017 (JP) .............................. JP2017-222882

(51) Int. Cl.
| | | |
|---|---|---|
| *A61B 5/00* | (2006.01) | |
| *A61B 5/18* | (2006.01) | |
| *B60K 28/06* | (2006.01) | |
| *B60W 40/08* | (2012.01) | |
| *B60W 60/00* | (2020.01) | |

(52) U.S. Cl.
CPC .............. *A61B 5/7239* (2013.01); *A61B 5/18* (2013.01); *A61B 5/6893* (2013.01); *A61B 5/7278* (2013.01); *B60K 28/06* (2013.01); *B60W 40/08* (2013.01); *B60W 60/0051* (2020.02); *B60W 60/0059* (2020.02)

(58) Field of Classification Search
None
See application file for complete search history.

(56) References Cited

U.S. PATENT DOCUMENTS

| | | | | |
|---|---|---|---|---|
| 9,704,403 | B2* | 7/2017 | Chen ................. | B60W 30/0956 |
| 9,725,036 | B1* | 8/2017 | Tarte ................... | B60K 28/066 |
| 2010/0109881 | A1* | 5/2010 | Eskandarian ........ | B60K 28/066 |
| | | | | 340/575 |
| 2014/0025257 | A1* | 1/2014 | Komoguchi ......... | B62D 15/025 |
| | | | | 701/36 |

(Continued)

FOREIGN PATENT DOCUMENTS

| | | |
|---|---|---|
| JP | 3-203412 | 9/1991 |
| JP | 6-197891 | 7/1994 |
| JP | 7-125560 | 5/1995 |

*Primary Examiner* — Dale W Hilgendorf
*Assistant Examiner* — Alexander C. Bost
(74) *Attorney, Agent, or Firm* — Fujitsu Patent Center

(57) ABSTRACT

An apparatus is configured to execute: a first process for estimating a first component at a first time point by using a waveform and the first component calculated from the waveform before the first time point, the waveform being based on a running trace of a vehicle, the first component being less than a first frequency; a second process for estimating the first component at the first time point by using the waveform, the first component calculated from the waveform before the first time point, and a second component at the first time point, the second component being greater than the first frequency and predicted from the second component calculated from the waveform before the first time point; and a calculation process for calculating the second component at the first time point from the waveform based on the first components estimated by the first and second process.

15 Claims, 34 Drawing Sheets

(56) References Cited

U.S. PATENT DOCUMENTS

| | | | |
|---|---|---|---|
| 2015/0039186 A1* | 2/2015 | Okuda | G08G 1/167 701/41 |
| 2015/0291095 A1* | 10/2015 | Chien | G08G 1/167 348/148 |
| 2016/0035220 A1* | 2/2016 | Paromtchik | B60W 40/09 701/117 |
| 2016/0129938 A1* | 5/2016 | Okuda | B62D 15/025 701/41 |
| 2016/0132054 A1* | 5/2016 | Eigel | B60W 50/16 701/23 |
| 2018/0111628 A1* | 4/2018 | Tamagaki | B60W 50/12 |
| 2018/0170424 A1* | 6/2018 | Tatsukawa | B62D 6/10 |
| 2018/0237007 A1* | 8/2018 | Adam | B60W 30/0953 |
| 2018/0268695 A1* | 9/2018 | Agnew | B60K 28/066 |
| 2019/0061759 A1* | 2/2019 | Tomishima | B62D 6/00 |
| 2019/0263368 A1* | 8/2019 | Takahashi | B60T 8/171 |

\* cited by examiner

FIG. 13
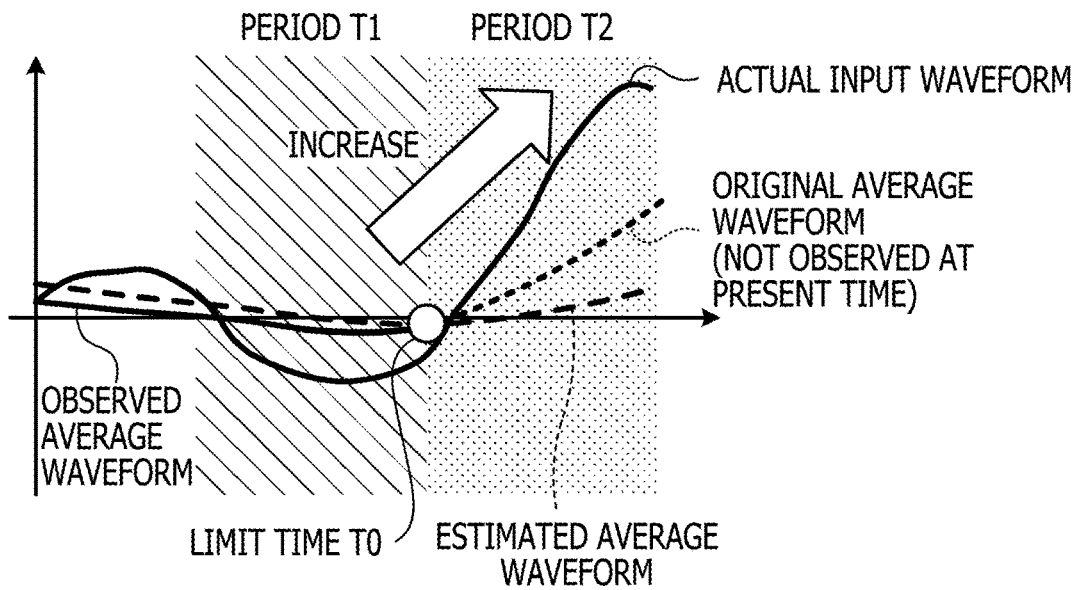
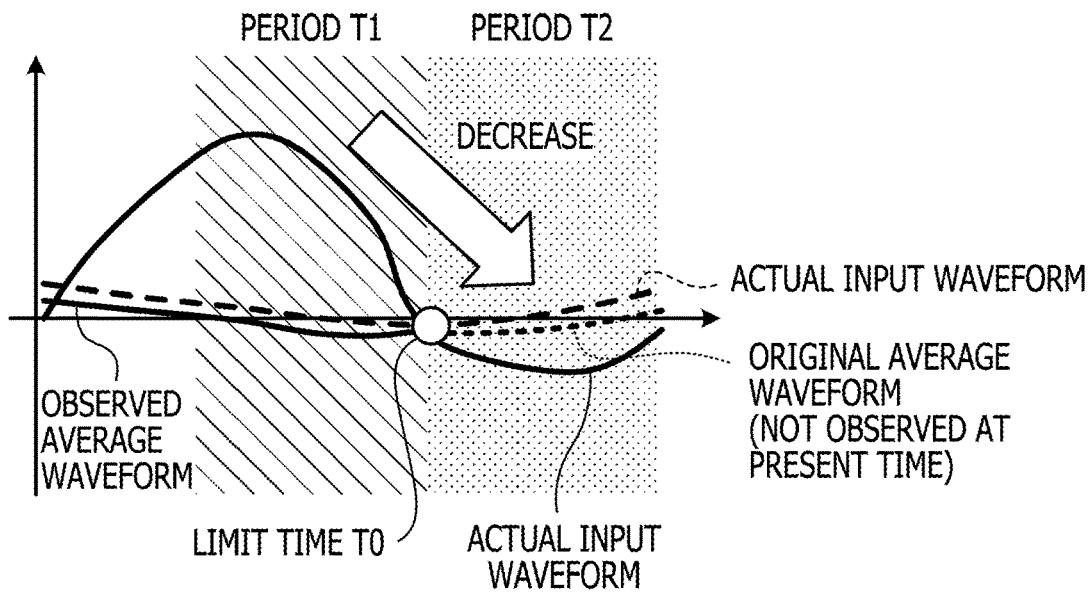

WAVEFORM ESTIMATION APPARATUS, WAVEFORM ESTIMATION METHOD, AND NON-TRANSITORY COMPUTER-READABLE STORAGE MEDIUM

CROSS-REFERENCE TO RELATED APPLICATION

This application is based upon and claims the benefit of priority of the prior Japanese Patent Application No. 2017-222882, filed on Nov. 20, 2017, the entire contents of which are incorporated herein by reference.

FIELD

The embodiments discussed herein are related to a waveform estimation apparatus, a waveform estimation method, and a non-transitory computer-readable storage medium.

BACKGROUND

Apparatuses and systems are known that assist a driver in driving a vehicle safely by: detecting a dangerous faltering behavior of the vehicle resulting from a decline in the driver's attention concentration on the driving while the vehicle is running; and feeding back to the driver. For example, a technique is known which decomposes a waveform depending on changes in the steering angle and lateral displacement with time into high- and low-frequency components, and determines that a driver is in a low awareness state when a power ratio obtained by dividing the low-frequency component by the high-frequency component is high.

Examples of the related art include Japanese Laid-open Patent Publication Nos. 7-125560, 6-197891, and 3-203412.

SUMMARY

According to an aspect of the embodiments, a waveform estimation apparatus includes: a memory; and a processor coupled to the memory and configured to execute a first estimation process that includes estimating a first vibration component at a first time point by using an input waveform and the first vibration component which is calculated from the input waveform before the first time point, the input waveform being a waveform based on a running trace of a vehicle which runs along a roadway, the first vibration component being less than a first frequency, execute a second estimation process that includes estimating the first vibration component at the first time point by using the input waveform, the first vibration component which is calculated from the input waveform before the first time point, and a second vibration component at the first time point, the second vibration component being a component equal to or greater than the first frequency and being predicted from the second vibration component which is calculated from the input waveform before the first time point, and execute a calculation process that includes calculating the second vibration component at the first time point from the input waveform based on the first vibration component estimated by the first estimation process and the first vibration component estimated by the second estimation process.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 13 is a diagram for explaining a characteristic of an input waveform orientation of the method A;

DESCRIPTION OF EMBODIMENTS

The above-mentioned technique has difficulty in estimating waveform components related to a steering action in real time, and accordingly in providing safe drive assistance in real time. For example, the above-mentioned technique requires displacement amount data to be accumulated for a long time of approximately 50 seconds to 80 seconds for the purpose of accurately estimate an awakening level, and accordingly takes a long time to perform signal processing for the purpose of classifying waveforms.

Based on the drawings, detailed descriptions will be hereinbelow provided for waveform estimators, waveform estimation methods, and waveform estimation programs according to embodiments disclosed by the present application. The embodiments do not limit the disclosure. The embodiments may be combined within an uncontradictory scope depending on the necessity.

Embodiment 1

(Overall Configuration)

Figure 1:
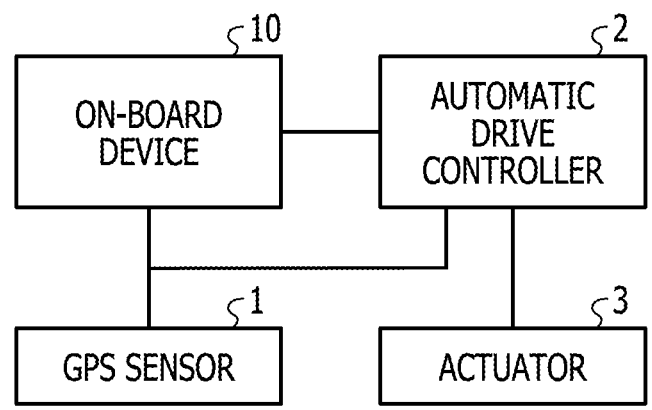
FIG. 1 is a functional block diagram illustrating a functional configuration of a running control system according to Embodiment 1.

FIG. 1 is a functional block diagram illustrating a functional configuration of a running control system according to Embodiment 1. As illustrated in FIG. 1, the running control system includes a Global Positioning System (GPS) sensor 1, an on-board device 10, an automatic drive controller 2, and an actuator 3. The running control system is mounted, for example, in a vehicle.

The GPS sensor 1 is a sensor mounted in the vehicle, and obtains positional information on the vehicle. The GPS sensor 1 outputs the obtained positional information to the on-board device 10 and the automatic drive controller 2.

The on-board device 10 is a computer mounted in the vehicle, and obtains the positional information from the GPS sensor 1 to generate a running trace and the like of the vehicle. On one hand, the on-board device 10 is capable of generating the running trace of the vehicle using a publicly-known method such as a white-line detection process. On the other hand, the on-board device 10 is capable of obtaining driving information on the vehicle to be used to generate the running trace using various publicly-known methods, the GPS sensor 1, and the like.

Based on the running trace of the vehicle and the driving information on the vehicle, the on-board device 10 evaluates how the driver is driving. For example, the on-board device 10 decomposes the waveform of the running trace into three component waveforms, that is to say, long-, intermediate- and short-cycle component waveforms. The long-cycle component waveform represents how largely the driver unwarily turns the steering wheel. The intermediate-cycle component waveform represents how largely the driver warily turns the steering wheel. The short-cycle component waveform represents how largely the driver abruptly turns the steering wheel. The on-board device 10 is capable of decomposing the waveform of the running trace into the component waveforms during a period up until the present time by estimating the composition waveforms from a half wavelength before each period through the present time. The on-board device 10 is, therefore, capable of reduce the amount of time it takes to perform the process (signal process) of decomposing the waveform of the running trace into the three component waveforms.

Thereafter, from the feature amounts of three respective component waveforms, the on-board device 10 evaluates an overall swing and an abrupt steering. Since the on-board device 10 is capable of decomposing the waveform of the running trace into the three component waveforms during the period up until the present time, the on-board device 10 is capable of evaluating the overall swing and the abrupt steering in real time. Thus, from results of the real-time evaluations, the on-board device 10 calculates how dangerously the vehicle is faltering. When the faltering level exceeds a threshold, the on-board device 10 determines that the vehicle is dangerously faltering. Accordingly, the on-board device 10 is capable of reducing the amount of time it takes to detect the dangerous faltering of the vehicle.

Figure 2:
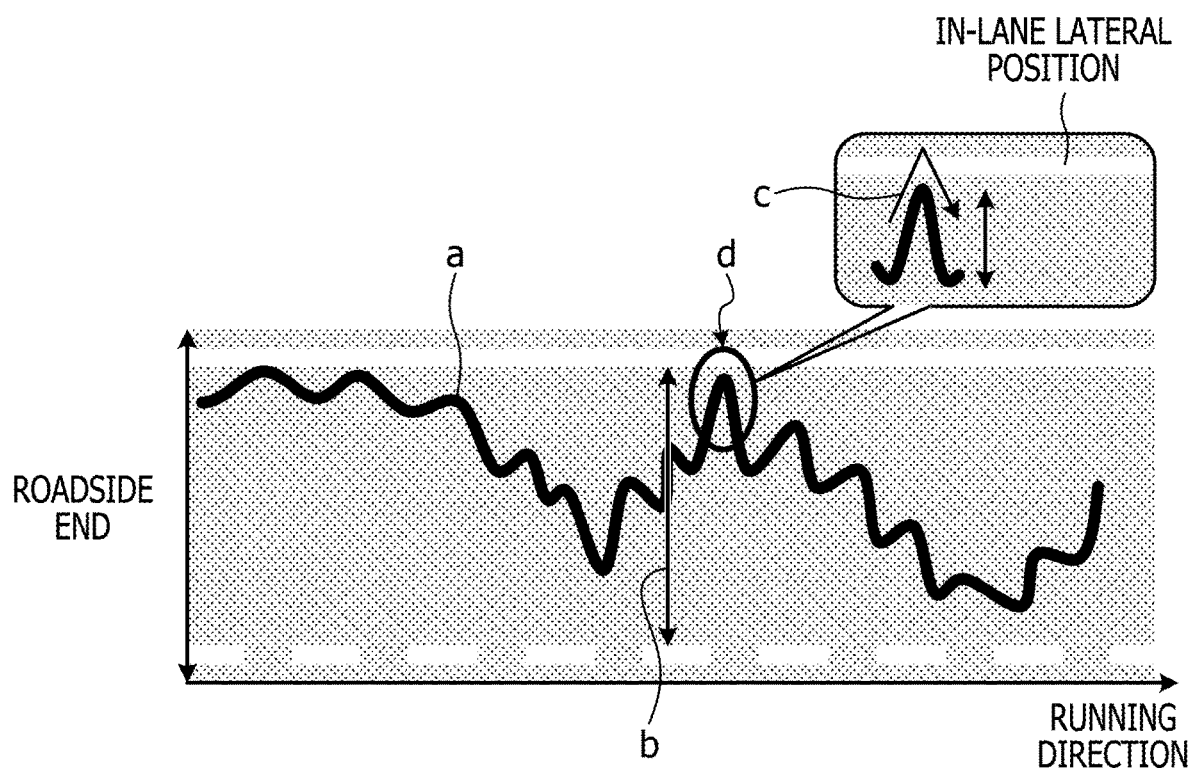
FIG. 2 is a diagram for explaining a running trace of a vehicle.

Descriptions will be provided for a relationship between the running trace and a detection point. FIG. 2 is a diagram for explaining the running trace of the vehicle. Let us assume that, as illustrated in FIG. 2, the vehicle is running along a lane between a white dashed line and a white solid line. When the vehicle runs beyond the dashed line or solid line, there occurs a danger such as the vehicle's collision with another vehicle which is running along another lane.

For example, in the running trace a illustrated in FIG. 2, the dangerous faltering is a situation in which: an overall swing (denoted by reference sign b in FIG. 2) is large; and an abrupt steering trace (denoted by reference sign c in FIG. 2) occurs in a roadside end (denoted by reference sign d in FIG. 2) and a swing end. The large overall swing means a decrease in concentration of awareness for keeping the lane. The abrupt steering trace means an abrupt response resulting from a response delay. The abrupt steering means a timing at which the driver turns the steering wheel in order to avoid the vehicle getting out of the lane. Evaluating these factors, the on-board device 10 determines how dangerously the vehicle is running. The on-board device 10 outputs the determination result to the automatic drive controller 2.

The automatic drive controller 2 is a computer mounted in the vehicle, and controls the automatic drive of the vehicle. For example, when the on-board device 10 determines that the vehicle is dangerously faltering, the automatic drive controller 2 switches the vehicle drive mode from a manual drive mode where the driver manually drives the vehicle to an automatic drive mode where the automatic drive controller 2 automatically drives the vehicle. The automatic drive controller 2 is capable of switching the drive modes, for example, based on an instruction from the driver. Once the automatic drive controller 2 switches the vehicle drive mode to the automatic drive mode, the automatic drive controller 2 controls the steering angle and the vehicle speed by controlling the actuator 3 based on the positional information from the GPS sensor 1 and the like. Thereby, the automatic drive controller 2 performs the automatic drive control in order to make the vehicle automatically run. The automatic drive controller 2 is capable of performing the automatic drive control of the vehicle using a publicly-known method such as the white line detection process.

The actuator 3 includes, for example, an acceleration actuator, a brake actuator and a steering actuator. The acceleration actuator adjusts the opening degree of the throttle valves in an engine. Based on an instruction from the automatic drive controller 2, the acceleration actuator adjusts the opening degree of the throttle valves. The brake actuator controls the rotation of the disks, drums and the like which rotate together with the wheels by applying hydraulic pressure to the wheel cylinders of the respective wheels. Based on an instruction from the automatic drive controller 2, the brake actuator adjusts the hydraulic pressure. The steering actuator provides steering toque to the steering mechanism. Based on an instruction from the automatic drive controller 2, the brake actuator adjusts the steering torque.

(Real-Time Determination)

Figure 3:
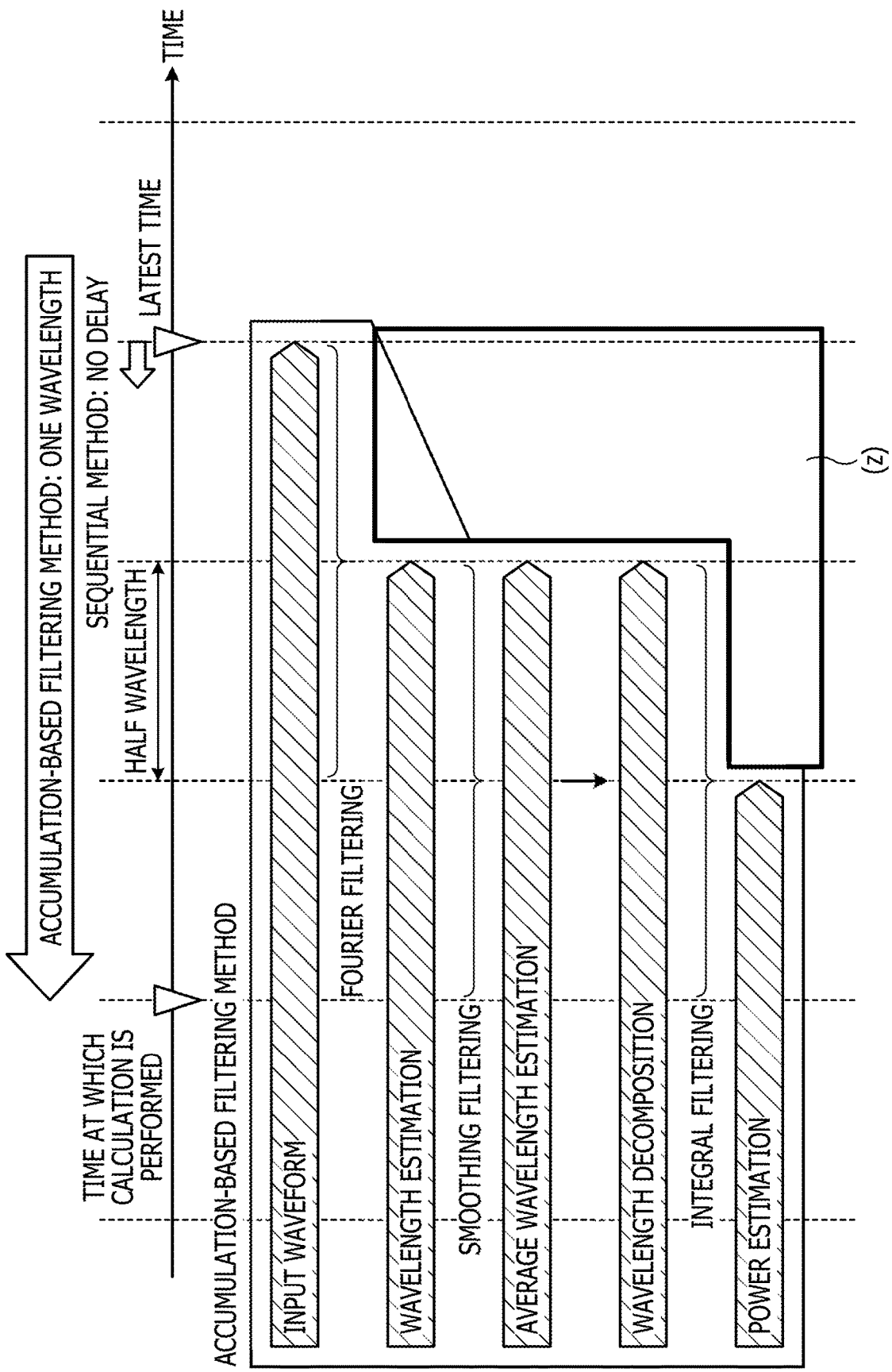
FIG. 3 is a diagram for explaining how to determine in real time whether driving is safe.

Next, descriptions will be provided for a method of determining in real time whether the driving is safe, which is performed by the on-board device 10. FIG. 3 is a diagram for explaining how to determine in real time whether the driving is safe. A generally-known safe drive determination method is an accumulation method of determining whether the driving is safe based on an accumulated running trace. For example, the accumulation method filters frequencies in order of a high frequency (slight steering vibration) to a low frequency (center swing) for the purpose of decomposing the running trace into the steering waveforms (swing components). From each input waveform, the accumulation method performs calculations for a wavelength estimation, an average wavelength estimation, a waveform decomposition, and a power calculation in this order by scanning the whole frame.

For example, from the input waveform, the accumulation method extracts an average waveform A and a swing waveform A. Using the swing waveform A, the accumulation method extracts a slight steering component which represents a slight steering correction, a noise and the like. From the average waveform A extracted from the input waveform, the accumulation method extracts an average waveform B and a swing waveform B. Using the swing waveform B, the accumulation method extracts a correction steering component which represents a main manipulation and the like for the steering. From the average waveform B, the accumulation method extracts an average waveform C and a swing waveform C. Using the swing waveform C, the accumulation method extracts an in-lane swing component which represents things such as a faltering run in the lane throughout the width of the lane. Using the average waveform C, the accumulation method extracts a center vibration component which represents a change in the center of the in-lane vibration. Thereby, from the input waveform, the accumulation method determines whether the driving is safe. The waveform decomposition means decomposition of a waveform into an average waveform and a swing waveform. The average waveform is used as an input for decomposing the waveform into an average waveform and a swing waveform each with a lower frequency. The swing waveform is used to calculate the power in a frequency band of interest.

As discussed above, for the swing waveform estimation, the accumulation method requires half wavelengths before and after the time of interest to be observed, and thus requires data on the half wavelength coming after the time of interest. The accumulation method is accordingly capable of estimating the swing waveform using only the accumulated data. The accumulation method, therefore, is incapable of perform the real-time analysis while the vehicle is running. For example, as illustrated in FIG. 3, waveform information corresponding to a region (z) is not available from the input waveform which is observed at the present time (latest time). For example, the waveform at time corresponding to a half wavelength before the present time is lacking for the wavelength estimation, the average waveform estimation and the waveform decomposition, as well as the waveform at time corresponding to one wavelength before the present time is lacking for the power estimation. For this reason, time delay occurs corresponding to the wavelength, and the determination that the vehicle is dangerously faltering is accordingly delayed. For example, the real-time safe drive determination requires the waveform decomposition to be performed in a frame-to-frame basis in chronological order instead of the accumulation basis, and also requires compensation for the delay in the filtering for the waveform decomposition.

(Waveform Estimation According to Embodiment 1)

Next, descriptions will be provided for the waveform estimation to be performed by the on-board device 10 according to Embodiment 1. As discussed above, the vibration component (average waveform) and the other vibration component (swing waveform) are extracted from the input waveform, and the waveform power is calculation using the swing waveform. Since the waveform at time corresponding to the half wavelength before the present time is lacking for the real-time safe drive determination, the waveform at time corresponding to the half wavelength before (the half wavelength immediately before) the present time has to be estimated. With this taken into consideration, Embodiment 1 estimates the waveform at time corresponding to a half wavelength immediately before the present time.

Figure 4A:
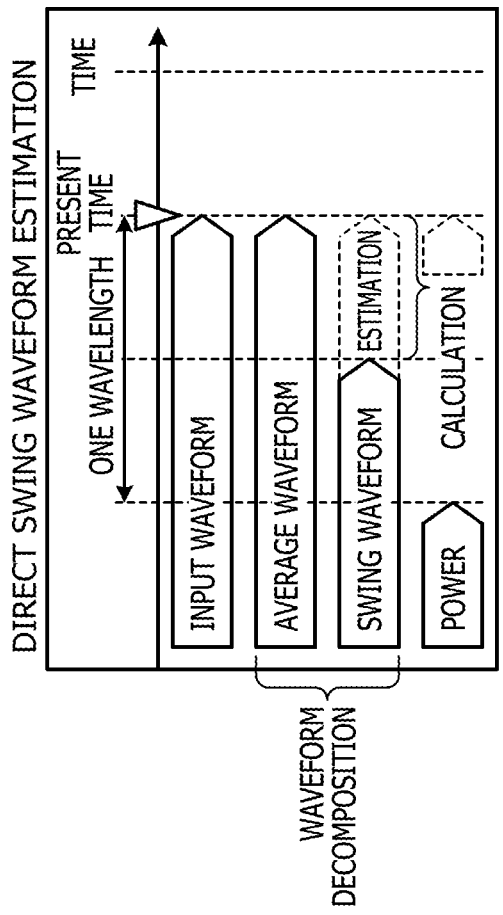
FIGS. 4A and 4B are diagrams for explaining how to estimate a waveform in Embodiment 1.
Figure 4B:
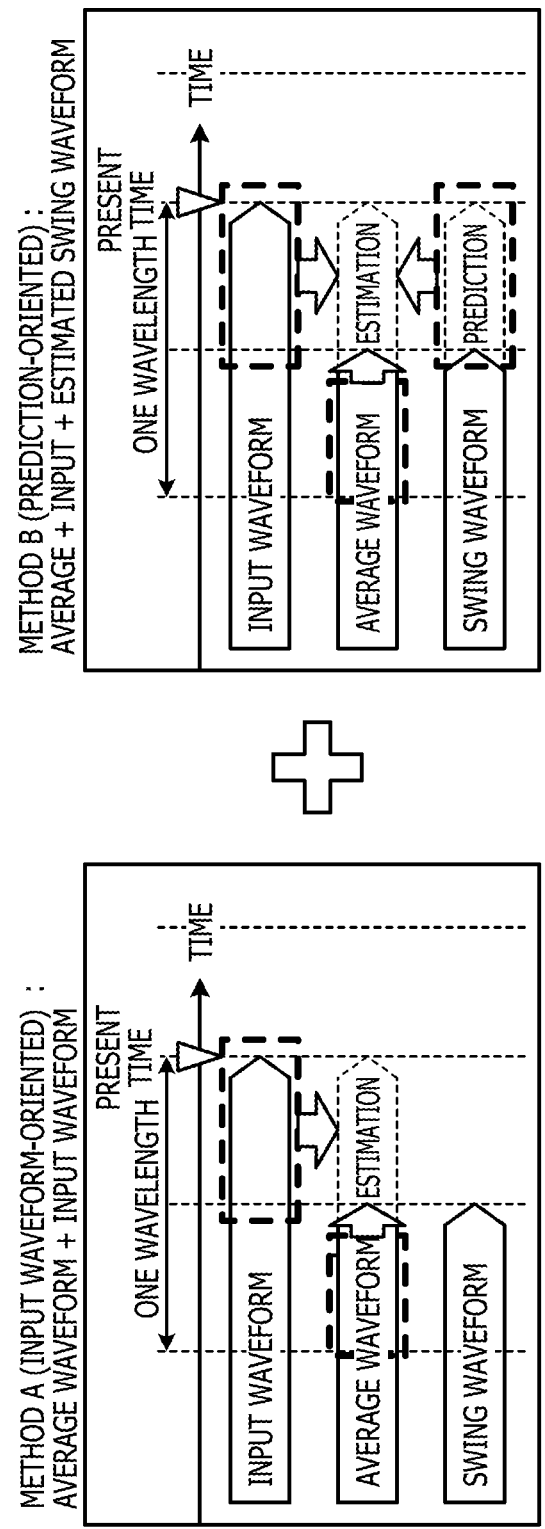

FIGS. 4A and 4B are diagrams for explaining how to estimate the waveform in Embodiment 1. To begin with, descriptions will be provided for an autoregressive model and an autoregressive moving average model. As illustrated in FIG. 4A, a general waveform estimation method estimates an incoming waveform by modeling the past waveform shape in chronological order, and thereby estimates the swing waveform directly.

However, the general method accumulates only a tendency during the period up until time corresponding to a half cycle before the present time, and accordingly does not reflect a tendency during a half cycle immediately before the present time. For this reason, when the tendency during the half wavelength (a half of the wavelength) immediate before the present time is different from the preceding waveform which is used for the estimation, the estimated shape corresponding to the half of the wavelength becomes different from the waveform shape around the present time to a large extent. A value obtained by estimating the waveform within the half of the wavelength where there is no input using the autoregressive moving average model indicates a behavior of converging to a constant, and accordingly does not represent the swing sufficiently. As discussed above, the general method does not estimate the waveform around the present time correctly.

In contrast to this, the on-board device 10 according to Embodiment 1 estimates an average waveform with the waveform decomposition method taken into consideration. For example, instead of directly estimating the swing waveform, the on-board device 10 calculates the swing waveform by: estimation the average waveform; and subtracting the estimated average waveform from the input waveform. To this end, as illustrated in FIG. 4B, the on-board device 10 according to Embodiment 1 employs a hybrid waveform estimation method obtained by combining a method A (input waveform-oriented) and a method B (prediction-oriented).

The method A (input waveform-oriented) estimates the average waveform during the period up until time corresponding to the half wavelength immediately before the present time using: a calculated input waveform during a period from time corresponding to a half wavelength before the present time through the present time; and a calculated average waveform during a period from time corresponding to one wavelength before the present time through time corresponding to the half wavelength before the present time. For example, the method A estimates the average waveform expressed with a linear expression (y1=a×t+b).

The method B (prediction-oriented) estimates an average waveform up until time corresponding to the half wavelength immediately before the present time using: the calculated input waveform during the period from time corresponding to the half wavelength before the present time through the present time; the calculated average waveform during the period from time corresponding to the one wavelength before the present time through time corresponding to the half wavelength before the present time; and a swing waveform at time corresponding to the half wavelength before the present time which is predicted from the calculated swing waveform during the period from time corresponding to the one wavelength before the present time through time corresponding to the half wavelength before the present time. For example, the method B estimates the average waveform expressed with a quadratic expression (y2=c×t$^2$+d×t+e).

The hybrid waveform estimation method adds up the average waveform estimated by the method A and the average waveform estimated by the method B, and thereby estimates an average waveform during the period from time corresponding to the half wavelength before the present time through the present time. For example, the hybrid waveform estimation method calculates a sum expressed with "y=0.5c×t$^2$+0.5×(a+d)×t+0.5×(b+e)" of the average waveform expressed with the linear expression (y1=a×t+b) and the average waveform expressed with the quadratic expression (y2=c×t$^2$+d×t+e).

Thereafter, the on-board device 10 estimates a swing waveform during the period from time corresponding to the half wavelength before the present time through the present time by subtracting the estimated average waveform from the input waveform. Subsequently, the on-board device 10 calculates a waveform power from the estimated swing waveform, and thereby performs a real-time safe drive determination. As discussed above, the on-board device 10 combines the method B good at the steady-state characteristic with the method A which exhibits the opposite characteristic when faced with increase and decrease changes in the swing, and thereby realizes the swing waveform estimation good at following the increase and decrease.

(Functional Configuration)

Figure 5:
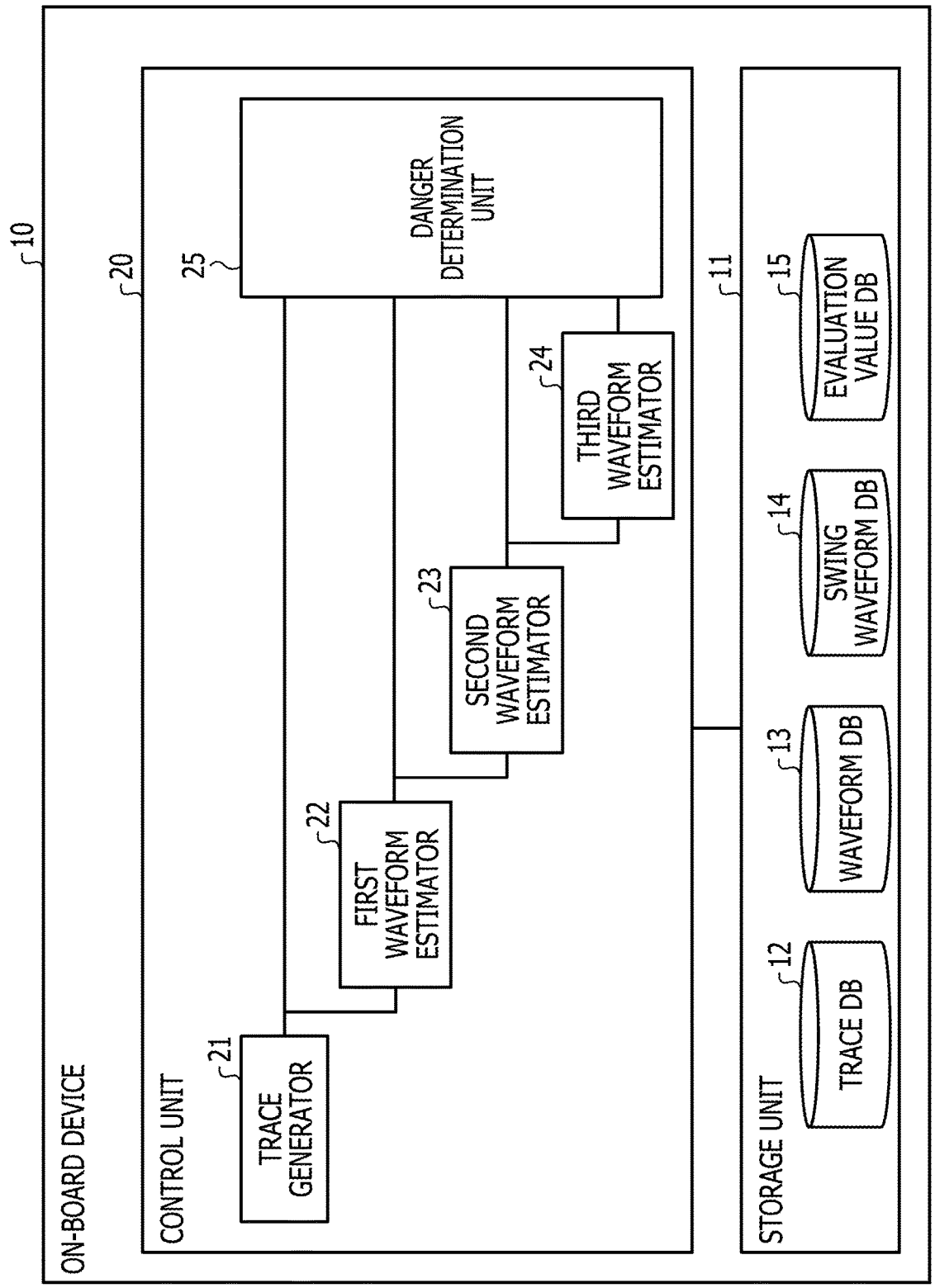
FIG. 5 is a functional block diagram illustrating a functional configuration of an automatic drive controller according to Embodiment 1.

FIG. 5 is a functional block diagram illustrating a functional configuration of the automatic drive controller 10 according to Embodiment 1. The automatic drive controller 2 is a computer which automatically drives the vehicle, and has the same function as a general automatic drive controller. Detailed descriptions will be omitted herein.

As illustrated in FIG. 5, the on-board device 10 includes a storage unit 11 and a control unit 20. The storage unit 11 is a storage which stores programs, data and the like. The storage unit 11 is, for example, a memory or a hard disk. The storage unit 11 stores a trace database (DB) 12, a waveform DB 13, a swing waveform DB 14, and an evaluation value DB 15. The trace DB 12 is a database which stores the running trace, the driving information and the like generated by the controller 20 in association with the time length for which the vehicle has run.

The waveform DB 13 stores the long-, intermediate- and short-cycle component waveforms (vibration components) into which the waveform of the running trace is decomposed. The waveform DB 13 is a database stores the component waveforms generated by the controller 20 in association with the time length for which the vehicle has run.

Figure 6:
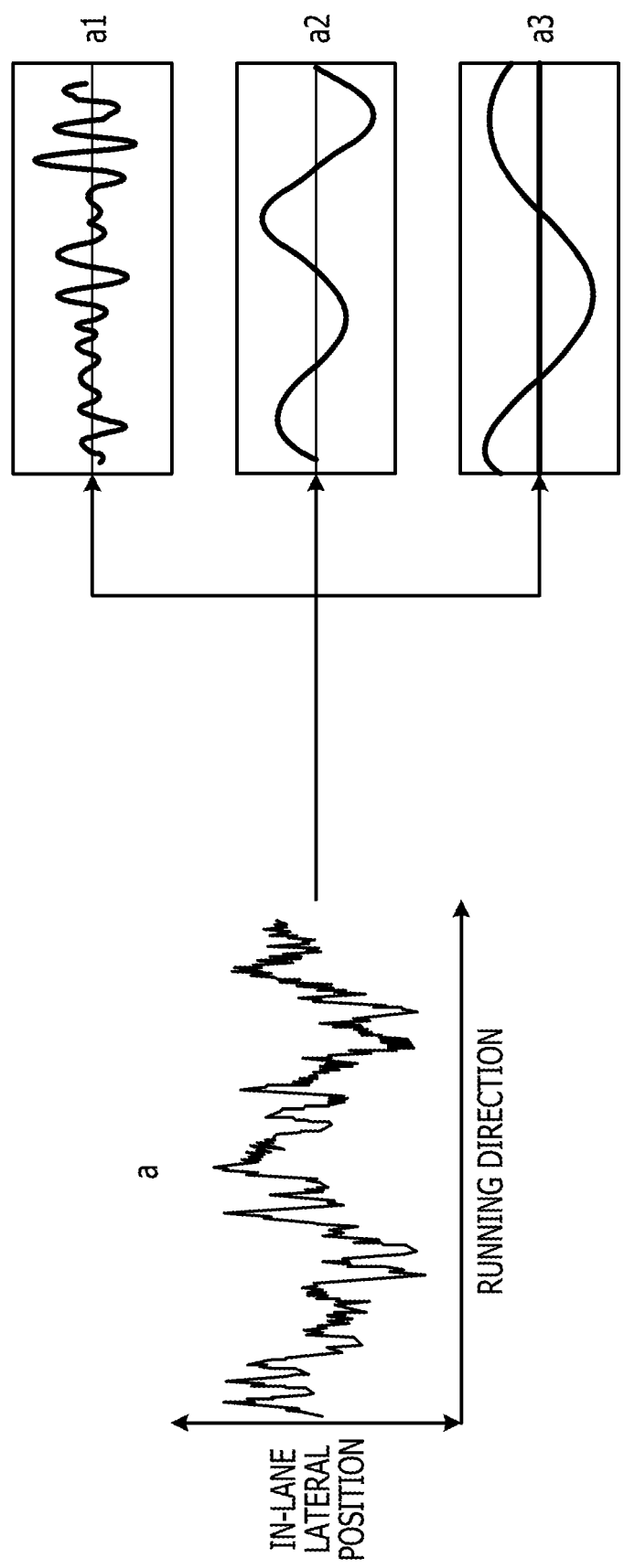
FIG. 6 is a diagram for explaining component waveforms of a running trace.

Descriptions will be provided for the component waveforms into which the waveform of the running trace is decomposed. FIG. 6 is a diagram for explaining the component waveforms of the running trace. As illustrated in FIG. 6, the waveform a of the running trace is decomposed into a vibration component a1 concerning a cycle-period abrupt steering, a vibration component a2 concerning an intermediate-cycle normal steering, and a vibration component a3 concerning a long-cycle in-lane swing. The periods of the respective vibration components a1 to a3 are different from one another at each point of time, but are within their respective predetermined ranges.

For example, the short-cycle component waveform includes a waveform with a period of 1 to 4 seconds; the intermediate-cycle component waveform includes a waveform with a period of 8 to 16 seconds; and the long-cycle component waveform includes a waveform with a period of 60 to 90 seconds. The cycle ranges are examples. The cycle ranges are not limited to these examples, as long as the cycle ranges do not overlap one another. The period lengths of the respective vibration components a1 to a3 at each point of time are determined, for example, as response components representing the target frequency ranges in a frequency domain represented by the discrete Fourier transform (DFT) into which the waveform of the running trace is transformed over a point of time of the extraction. Each response period (frequency) may be determined using a frequency (period) which illustrates the largest response in the corresponding frequency range, or using a statistical amount such as an average or median value in the corresponding frequency range.

The swing waveform DB 14 is a database which stores swing waveforms calculated in the past. The swing waveform DB 14 stores, for example, swing waveforms corresponding respectively to short-, intermediate- and long-cycle component waveforms which are obtained from the measured running trace.

The evaluation value DB 15 is a database which stores danger degree evaluation results. The evaluation DB 15 stores, for example, evaluation values in association with the time length for which the vehicle has run. The evaluation values are values representing evaluations depending on the running trace. A higher numerical value represents a more dangerous drive.

The controller 20 is a processor which controls all the other parts of the on-board device 10, and is for example a processor. The controller 20 includes a trace generator 21, a first waveform estimator 22, a second waveform estimator 23, a third waveform estimator 24, and a danger determination unit 25. The trace generator 21, the first waveform estimator 22, the second waveform estimator 23, the third waveform estimator 24, and the danger determination unit 25 are examples of electronic circuits in a processor or the like, or examples of processes to be performed by the processor.

The trace generator 21 is a processor which generates the running trace of the vehicle based on the positional information obtained from the GPS sensor 1. The trace generator 21 is also capable of generating the running trace of the vehicle by receiving information or the like about an image captured by a drive recorder or the like while the vehicle is running, and using the white line detection process or the like. The trace generator 21 stores the generated running trace onto the trace DB 12.

The first to third waveform estimators 22 to 24 are processing units which decomposes the waveform of the running trace into the short-, intermediate- and long-cycle component waveforms (vibration components a1 to a3) from the run starting time through the present time. The first waveform estimator 22 uses the waveform of the running trace as the input waveform, and decomposes the waveform of the running trace into the short-cycle vibration component a1 (a first swing waveform) and the other vibration component (a first average waveform). The first waveform estimator 22 further calculates the waveform power of the short-cycle vibration component a1. Detailed descriptions of the process to be performed by the first waveform estimator 22 will be omitted.

Thereafter, the second waveform estimator 23 uses the first average waveform decomposed by the first waveform estimator 22 as the input waveform, and decomposes the first average waveform into the intermediate-cycle vibration component a2 (a second swing waveform) and the other vibration component (a second average waveform). The second waveform estimator 23 further calculates the waveform power of the intermediate-cycle vibration component a2. The third waveform estimator 24 uses the second average waveform decomposed by the second waveform estimator 23 as the input waveform, and decomposes the second average waveform into the low-period vibration component a3 (a third swing waveform). The third waveform estimator 24 further calculates the waveform power of the low-period vibration component a3. As discussed above, the first to third waveform estimators 22 to 24 decompose the waveform of the running trace into the high- to low-frequency vibration components a1 to a3 in this order.

Figure 7:
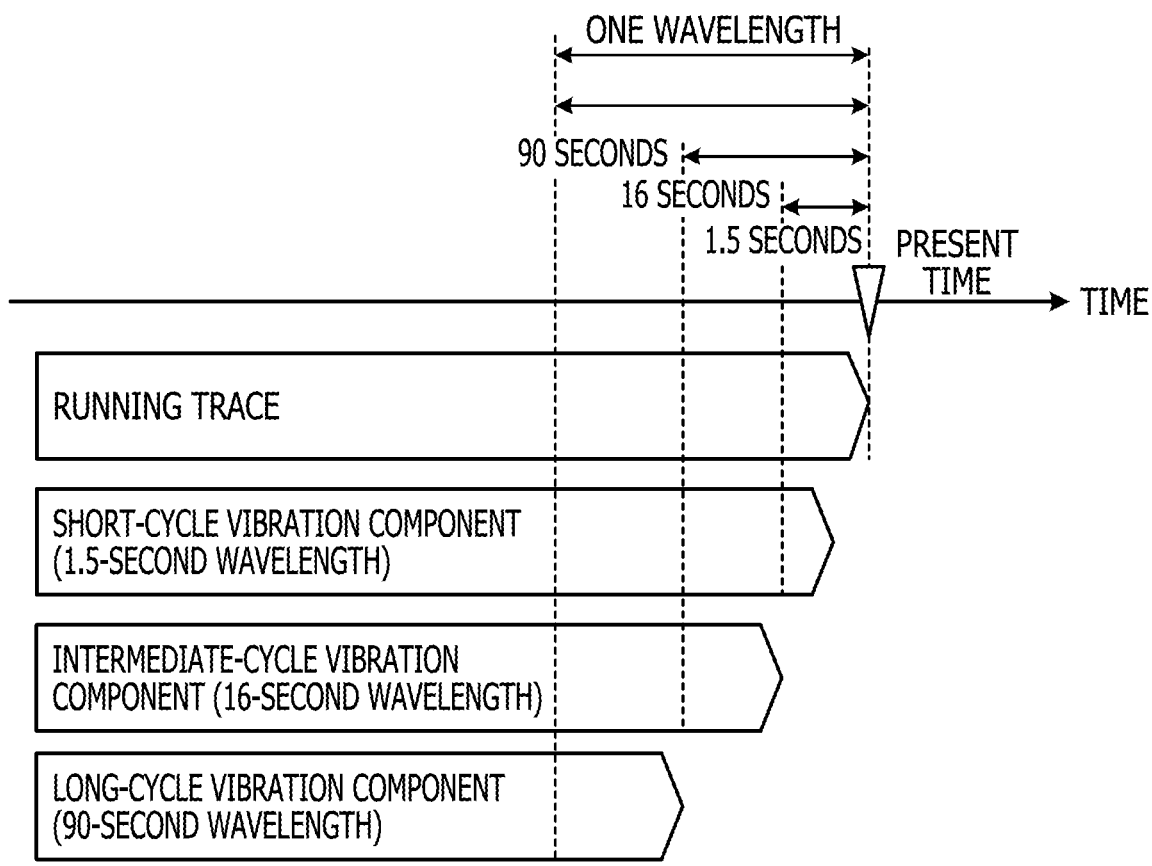
FIG. 7 is a diagram for explaining when to extract each vibration component.

Descriptions will be provided for when the vibration components a1 to a3. FIG. 7 is a diagram for explaining when to extract the vibration components a1 to a3. FIG. 7 schematically illustrates wavelengths of the respective vibration components a1 to a3. The first to third waveform estimators 22 to 24 decompose the waveform of the running trace into the vibration components a1 to a3 by transforming the respective input waveforms each with one wavelength into the frequency domain mainly around the point of time of the extraction. The first to third waveform estimators 22 to 24, therefore, is capable of decomposing the waveform of the running trace directly into the vibration components a1 to a3 during the period up until time corresponding to the half wavelength before the present time. However, the first to third waveform estimators 22 to 24 are incapable of decomposing the waveform of the running trace directly into the vibration components a1 to a3 during the period from time corresponding to the half wavelength before the present time through the present time. For example, in a case where the sort cycle is 1.5 seconds, the first to third waveform estimators 22 to 24 are incapable of decomposing the waveform of the running trace into the vibration components a1 to a3 during the period up until 0.25 seconds before the present time. For example, in a case where the intermediate cycle is 16 seconds, the first to third waveform estimators 22 to 24 are incapable of decomposing the waveform of the running trace into the vibration components a1 to a3 during the period up until 8 seconds before the present time. For example, in a case where the long cycle is 90 seconds, the first to third waveform estimators 22 to 24 are incapable of decomposing the waveform of the running trace into the vibration components a1 to a3 during the period up until 45 seconds before the present time.

As discussed above, the first to third waveform estimators 22 to 24 have to wait for a time length corresponding to the half wavelength to pass before the first to third waveform estimators 22 to 24 starts to decompose the waveform of the running trace directly into the vibration components a1 to a3. Thus, as long as the later-discussed danger determination unit 25 uses the vibration components a1 to a3 into which the waveform of the running trace is directly decomposed by the first to third waveform estimators 22 to 24, the dangerous faltering determination which the danger determination unit 25 performs is limited to a dangerous faltering determination during the period up until 90 seconds before the present time. Thus, the determination is not performed in real time. With this taken into consideration, Embodiment 1 is configured such that the first to third waveform estimators 22 to 24 are capable of performing the real-time vibration component decomposition by estimating the vibration components a1 to a3 during the period up until time corresponding to the half wavelength before the present time. This makes it possible for the dangerous faltering determination unit 25 to perform the dangerous faltering determination in real time.

(Functional Blocks of Wave Estimators)

Figure 8:
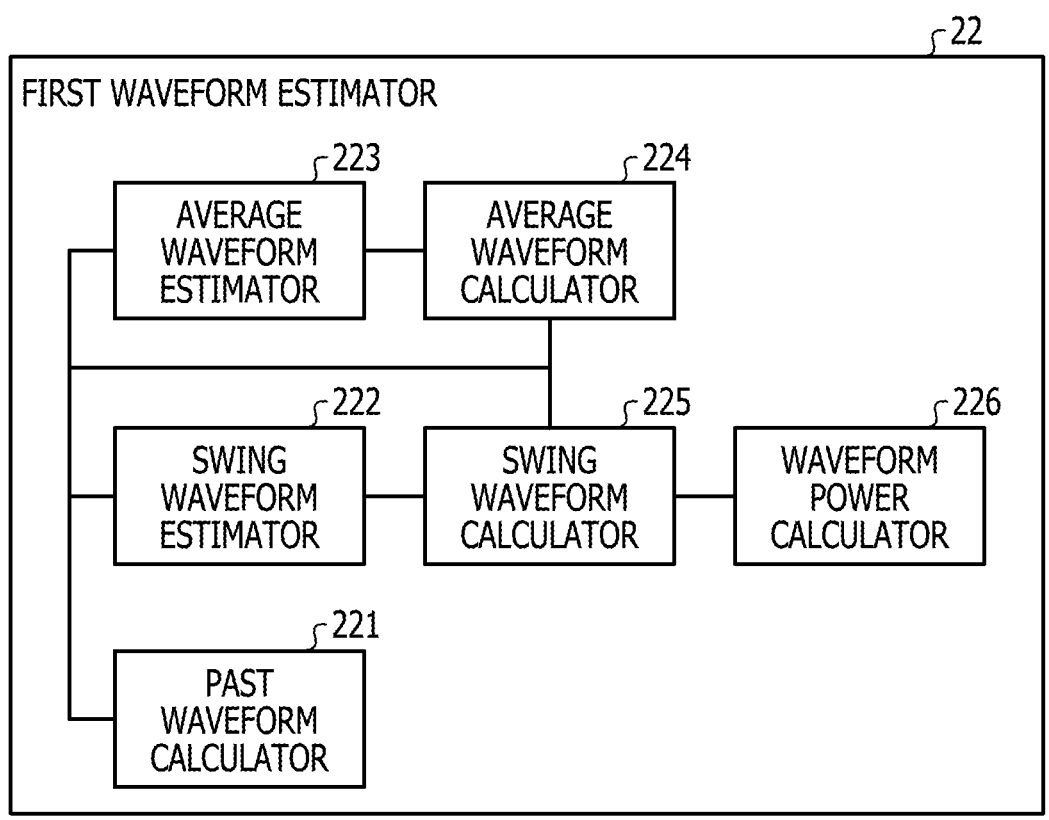
FIG. 8 is a functional block diagram illustrating a functional configuration of a first waveform estimator.

FIG. 8 is a functional block diagram illustrating a functional configuration of the first waveform estimator 22. The second and third waveform estimators 23, 24 perform the same process as the first waveform estimator 22 except that the period of the input waveform and the vibration components obtained by decomposition in each of the second and third waveform estimators 23, 24 are different from those in the first waveform estimator 22, and detailed descriptions for the second and third waveform estimators 23, 24 will be omitted.

As illustrated in FIG. 8, the first waveform estimator 22 includes a past waveform calculator 221, a swing waveform predictor 222, an average waveform estimator 223, an average waveform calculator 224, a swing waveform calculator 225, and a waveform power calculator 226. The past waveform calculator 221 is an example of a vibration calculator. The swing waveform predictor 222 is an example of an estimator. The average waveform estimator 223 and the average waveform calculator 224 are examples of a first estimator and a second estimator, respectively. The swing waveform calculator 225 is an example of a calculator.

The past waveform calculator 221 is a processor which decomposes the input waveform (the waveform of the running trace) into the first swing waveform (vibration component) and the first average waveform during the period up until time corresponding to the half wavelength before the present time. For example, for all the n wavelength candidates Lc={L1, L2, . . . , Ln}, the past waveform calculator 221 subjects the input waveform mainly around time corresponding to the half wavelength before the present time. Thereafter, the past waveform calculator 221 determines a wavelength which makes the vector size of the Fourier transform coefficients, or the sine value and the cosine value, largest as the waveform at time corresponding to the half wavelength before the present time.

Subsequently, the past waveform calculator 221 calculates the first average waveform by averaging the input waveforms over the determined wavelength range. The past waveform calculator 221 calculates the swing waveform (vibration component) by subtracting the calculated first average waveform from the input waveform during the period up until time corresponding to the half wavelength before the present time. The past waveform calculator 221 calculates the root mean square (RMS) value of the first swing waveforms mainly around time corresponding to the one wavelength before the present time over the wavelength range which is determined at the time, and sets the calculated RMS value as the waveform power. The past waveform calculator 221 stores the determined wavelength, the first swing waveform (vibration component) and the first average waveform obtained by the waveform decomposition, as well as the waveform power, onto the waveform DB 13. The past waveform calculator 221 also stores the determined wavelength, and the first swing waveform (vibration component) obtained by the waveform decomposition, onto the swing waveform DB 14.

The swing waveform predictor 222 is a processor which predicts the first swing waveform at the present time using the past first waveform calculated by the past waveform calculator 221. For example, from the swing waveform DB 14, the swing waveform predictor 222 obtains the first swing waveform during the period T1 from time corresponding to the one wavelength before the present time through time corresponding to the half wavelength before the present time, and identifies the amplitude and phase of the waveform. Thereafter, based on the identified amplitude and phase, the swing waveform predictor 222 predicts the first swing waveform during the period T2 from time corresponding to the half wavelength before the present time through the present time (during the period T2 corresponding the half wavelength immediately before the present time). Subsequently, the swing waveform predictor 222 outputs the predicted first swing waveform during the period T2 to the average waveform estimator 223 and the like.

The average waveform estimator 223 is a processor which estimates the first average waveform during the period T2 using the method A (input waveform-oriented) and the method B (prediction-oriented). For example, the average waveform estimator 223 calculates a parameter expressed with a polynomial expression which represents the first average waveforms in the respective methods.

(Explanation of Input Waveform-Oriented Method A)

Figure 9:
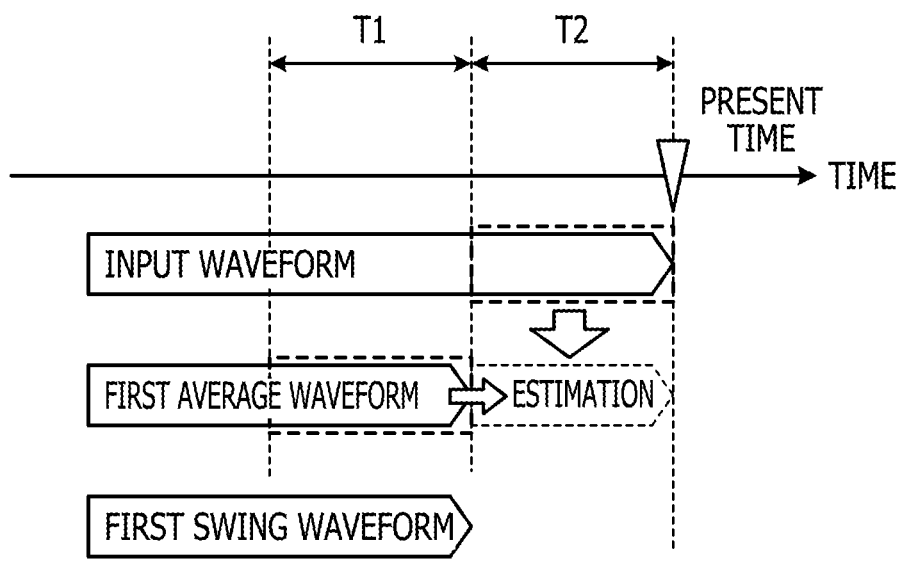
FIG. 9 is a diagram for explaining how to estimate a first average waveform using a method A.

FIG. 9 is a diagram for explaining how to estimate a first average waveform using the method A. As illustrated in FIG. 9, the average waveform estimator 223 estimates the first average waveform during the period T2 using the input waveform during the period T2, and the first average waveform during the period T1. This makes it possible for the average waveform estimator 223 to estimate the first average waveform more accurately.

Figure 10:
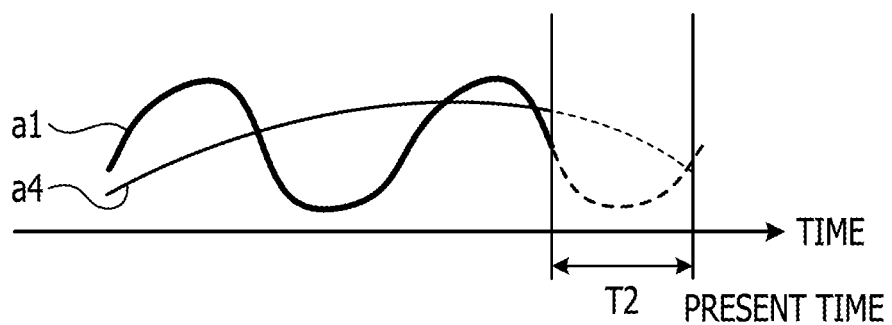
FIG. 10 is a diagram for explaining how to estimate the first average waveform.

Explanation will be provided for why the average waveform estimator 223 estimates the first average waveform parameter. FIG. 10 is a diagram for explaining how to estimate the first average waveform. In FIG. 10, the period of the first swing waveform (vibration component) a1 is four times as short as that of the first average waveform a4. Accordingly, the wavelength segment of the first average waveform a4 during the period from time corresponding to the short-cycle half wavelength before the present time through the present time (during the period T2) is approximately one eighth of the whole wavelength of the first average waveform a4, while the wavelength segment of the vibration component a1 during the period T2 is approximately one half of the whole wavelength of the vibration component a1. Thus, the first average waveform a4 during the period T2 may be modeled using a polynomial expression which represents monotonous increase and decrease. The first average waveform a4 during the period T2 may be modeled using a low-order polynomial expression expressed with $$y1_t = a \cdot t + b \quad (1)$$

where $y1_t$ is the position of the first average waveform at time t, as well as a and b are parameters. Time corresponding to the half wavelength before the present time is the reference (t=0). The present time is time corresponding to a half of the short cycle Ts (t=$T_s$/2). The parameter b is the first average waveform $y1_0$ when t=0. In this case, the actual average waveform position $m_0$ at the time t=0 corresponding to the half wavelength before the present time is calculated based on $$m_0 = a \cdot 0 + b$$

$$\hat{b} = m_0 \quad (2)$$

When t=0, the first average waveform $y1_0$ is obtained from the first average waveform $m_t$ which is calculated by the past waveform calculator 221 ($y1_0 = m_0$).

The average waveform estimator 223 calculates the parameter a in Equations 1 such that the parameter a minimizes the difference between the first average waveform $y1_t$ and the input waveform $p_t$ during the period T2. The average waveform estimator 223 further calculates the parameter a such that the parameter a minimizes the difference between the first average waveform $y1_t$ and the first average waveform $m_t$ calculated by the past waveform calculator 221 during the period T1 from the reference time t=0 through time corresponding to the half wavelength before the present time. For example, the average waveform estimator 223 calculates the difference between the first average waveform $y1_t$ and the input waveform $q_t$ using $$s_t = (y1_t - q_t) = (a \cdot t + m_0 - q_t). \quad (3)$$

The waveform $q_t$ is the input waveform $p_t$ when t≥0, and is the first average waveform $m_t$ calculated by the past waveform calculator 221 when t<0, as indicated by $$q = \begin{cases} m_t (t > 0) \\ p_t (t \geq 0) \end{cases} \quad (4)$$

Subsequently, the average waveform estimator 223 calculates a squared residual sum S of residuals $s_t$ based on $$S = (\tfrac{1}{2})\Sigma s_t^2 = (\tfrac{1}{2})\Sigma(a \cdot t + m_0 - q_t)^2 \quad (5)$$

and solves $$dS/db = \Sigma((a \cdot t + m_0 - q_t) \cdot t) = a\Sigma t^2 + \Sigma(m_0 - q_t)t = 0 \quad (6)$$

such that the squared residual sum S is minimized. Thereby, the average waveform estimator 223 calculates the parameter a, as indicated by $$\hat{a} = -\frac{\sum (m_0 - q_t) t}{\sum t^2} \quad (7)$$

The range of the integration ranges from −L/2 to L/2 where L (seconds) is the wavelength time.

As discussed above, the average waveform estimator 223 estimates the first average waveform $y1_t$ during the period T2 using the input waveform $p_t$ during the period T2 and the first average waveform $m_t$ during the period T1. In this manner, the average waveform estimator 223 calculates the coefficients in the polynomial expression model which minimizes the difference among the first average waveform during the period T2, the input waveform during the period T2, and the first average waveform during the period T1.

(Explanation of Prediction-Oriented Method B)

Figure 11:
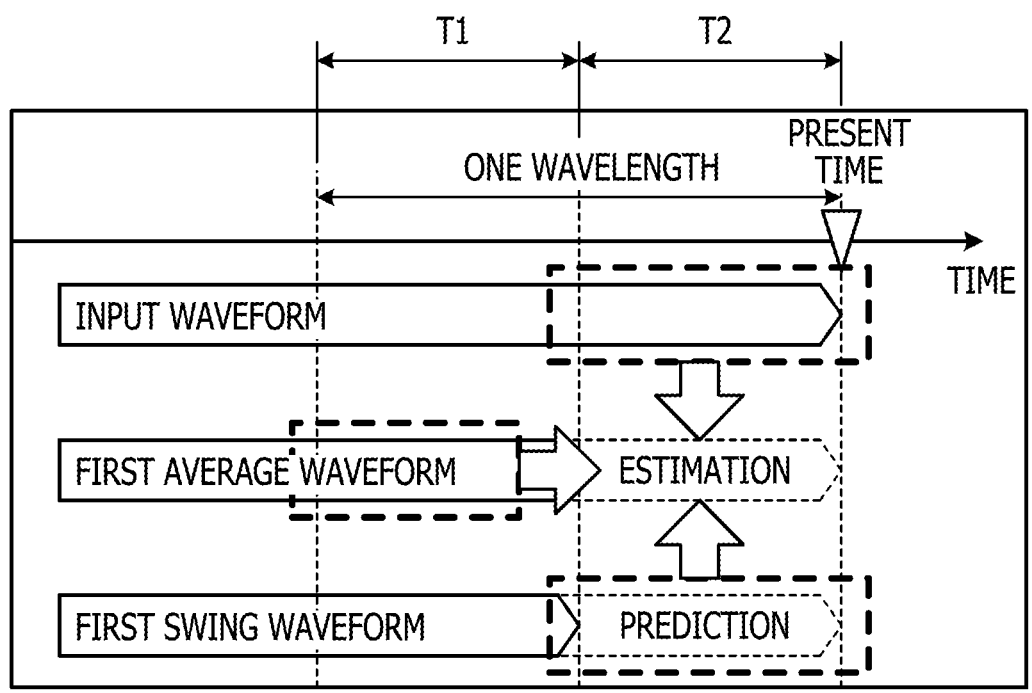
FIG. 11 is a diagram for explaining how to estimate the first average waveform using a method B.

FIG. 11 is a diagram for explaining how to estimate the first average waveform using the method B. As indicated by FIG. 11, the average waveform estimator 223 estimates the first average waveform during the period T2 using the observed input waveform during the period T2, the calculated first average waveform during the period T1, and the first swing waveform which is predicted from the calculated swing waveform during the period time T1. Thereby, the average waveform estimator 223 estimates the first average waveform more accurately.

Like in the method A, in the method B, the wavelength segment of the first average waveform a4 during the period from time corresponding to the short-cycle half wavelength before the present time through the present time (during the period T2) is approximately one eighth of the whole wavelength of the first average waveform a4, while the wavelength segment of the vibration component a1 during the period T2 is approximately one half of the whole wavelength of the vibration component a1. Thus, the first average waveform a4 during the period T2 may be modeled using a polynomial expression which represents monotonous increase and decrease. The first average waveform a4 during the period T2 may be modeled using a low-order polynomial expression expressed with $$y2_t = c \cdot t^2 + d \cdot t + e \quad (8)$$

where $y2_t$ is the position of the first average waveform at time t, as well as c, d and e are parameters.

Time corresponding to the half wavelength before the present time is the reference (t=0). The present time is time corresponding to a half of the short cycle Ts ($t=T_s/2$). The parameter e is the first average waveform $y2_0$ when t=0. In this case, the actual average waveform position $m_0$ at the time t=0 corresponding to the half wavelength before the present time is calculated based on $$m_0 = c \cdot 0^2 + d \cdot 0 + e$$

$$\hat{e} = m_0 \quad (2)$$

When t=0, the first average waveform $y2_0$ is obtained from the first average waveform $m_t$ which is calculated by the past waveform calculator 221 ($y2_0 = m_0$).

The swing waveform estimator 222 estimates the swing waveform at time t (t≥0) using $$u_t = A \cdot \sin(w \cdot t + B) \quad (10)$$

where A and B are respectively the amplitude and the phase of the input waveform at the reference time t=0.

Like in the method A, the average waveform estimator 223 calculates the parameters c, d in Equations 8 such that the parameters c, d minimize the difference between the first average waveform $y2_t$ and the input waveform $p_t$ during the period T2. The average waveform estimator 223 further calculates the parameters c, d such that the parameters c, d minimize the difference between the first average waveform $y2_t$ and the first average waveform $m_t$ calculated by the past waveform calculator 221 during the period T1 from the reference time t=0 through time corresponding to the half wavelength before the present time. For example, the average waveform estimator 223 calculates the difference between the first average waveform $y2_t$ and the input waveform $q_t$ using $$S_t = (y2_t - q_t) = (c \cdot t^2 + d \cdot t + m_0 - q_t) \quad (11)$$

The waveform $q_t$ is the input waveform $p_t - u_y$ when t≥0, and is the first average waveform $m_t$ calculated by the past waveform calculator 221 when t<0, as indicated by $$q_t = \begin{cases} m_t & (t < 0) \ldots \text{actual average waveform} \\ p_t - u_t & (t \geq 0) \ldots \text{estimated average waveform} \\ & (\text{input} - \text{estimated swing}) \end{cases} \quad (12)$$

where $m_t$ (t<0) is the actual average waveform, and $p_t - u_t$ (t≥0) is the predicted average waveform (input—predicted swing).

Subsequently, the average waveform estimator 223 calculates a squared residual sum S of residuals $s_t$ based on $$S = (1/2)\Sigma s_t^2 = (1/2)\Sigma(c \cdot t^2 + d \cdot t + m_0 - q_t)^2 \quad (13)$$

and solves $$dS/dc = \Sigma((c \cdot t^2 + d \cdot t + m_0 - q_t) \cdot t^2) = c\Sigma t^4 + d\Sigma t^3 + \Sigma(m_0 - q_t)$$
$$t^2 = 0 \quad (14)$$

and $$dS/dd = \Sigma((c \cdot t^2 + d \cdot t + m_0 - q_t) \cdot t) = c\Sigma t^3 + d\Sigma t^2 + \Sigma(m_0 - q_t)t = 0 \quad (15)$$

such that the squared residual sum S is minimized. Thereby, the average waveform estimator 223 calculates the parameters c, d, as indicated by $$\begin{pmatrix} \hat{c} \\ \hat{d} \end{pmatrix} = \begin{pmatrix} \sum t^4 & \sum t^3 \\ \sum t^3 & \sum t^2 \end{pmatrix}^{-1} \begin{pmatrix} -\sum (m_0 - q)t^2 \\ -\sum (m_0 - q)t \end{pmatrix} \quad (16)$$

The range of the integration ranges from $-L/2$ to $L/2$ where L (seconds) is the wavelength time.

As discussed above, the average waveform estimator 223 estimates the first average waveform $y2_t$ during the period T2 using the input waveform $p_t$ during the period T2, the predicted swing waveform $u_t$ during the period T2, and the first average waveform $m_t$ during the period T1. Thereafter, the average waveform estimator 223 outputs the calculated parameters to the average waveform calculator 224.

The average waveform calculator 224 is a processor which calculates the first average waveform $y_t$ during the period T2 based on the parameters a to e calculated by the average waveform estimator 223. For example, the average waveform calculator 224 calculates the first average waveform $y_t$ during the period T2 using the first average waveform $y1_t$ estimated by the method A, and the first average waveform $y2_t$ estimated by the method B. That is, the average waveform calculator 224 performs the hybrid waveform estimation.

For example, the average waveform calculator 224 generates $$y_t = \frac{y1_t + y2_t}{2} = \frac{\hat{c} \cdot t^2 + (\hat{a} + \hat{d}) \cdot t + (\hat{b} + \hat{e})}{2} \quad (17)$$

by adding up Equation 1 in which the calculated parameters a, b are set, and Equation 2 in which the calculated parameters c, d, e are set. Thereafter, the average waveform calculator 224 outputs the first average waveform $y_t$ during the period T2, calculated using Equation 17, to the swing waveform calculator 225.

Figure 12:
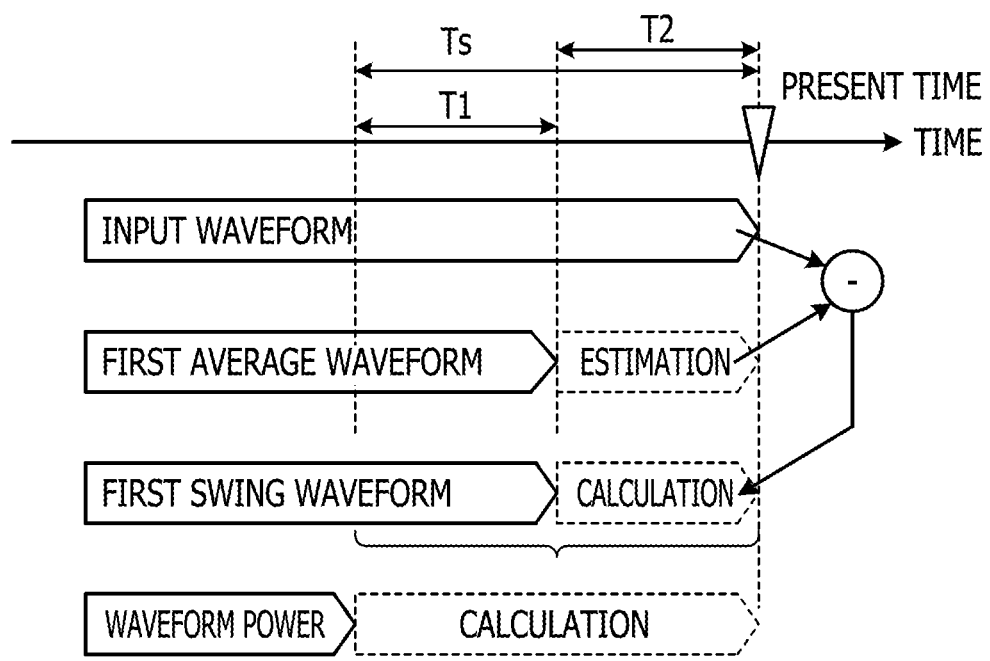
FIG. 12 is a diagram for explaining how to calculate a first swing waveform.

The swing waveform calculator 225 is a processor which calculates the first swing waveform as the vibration component during a period Ts based on the first average waveform $y_t$ obtained from the average waveform estimator 223. FIG. 12 is a diagram for explaining how to calculate the first swing waveform. As illustrated in FIG. 12, the swing waveform calculator 225 calculates the first swing waveform $r_t$ during the period T2 by subtracting the first average waveform $y_t$ during the period T2, calculated by the average waveform calculator 224, from the observed input waveform $p_t$ during the period T2. For example, the swing waveform calculator 225 calculates the first swing waveform $r_t$ during the period T2 based on $$r_t = p_t - y_t = p_t - \left( \frac{\hat{c} \cdot t^2 + (\hat{a} + \hat{d}) \cdot t + (\hat{b} + \hat{e})}{2} \right) \quad (18)$$

The waveform power calculator 226 is a processor which calculates the waveform power from the first swing waveform $r_t$ as the vibration component. For example, as illustrated in FIG. 12, the waveform power calculator 226 calculates the waveform power based on the first swing waveform during the period Ts (T1+T2). For example, the waveform power calculator 226 calculates the waveform power using the calculated first swing waveform during the period T1, and the first swing waveform predicted by the swing waveform calculator 226.

For example, the waveform power calculator 226 calculates the RMS value of the first swing waveforms $r_t$ during the period up until time corresponding to the one wavelength before the present time using $$POW = (1/t_c) \Sigma_{t=0}^{t_c} r_t^2 \quad (19)$$

The calculated RMS is used as the waveform power POW. Incidentally, $t_c = L/2$ where L(s) is the wavelength of interest. Thereafter, the waveform power calculator 226 outputs the calculated waveform power to the danger determination unit 25.

The second and third waveform estimators 23, 24 are similar to the first waveform estimator 22. The first waveform estimator 22 includes the past waveform calculator 221, the swing waveform predictor 222, the average waveform estimator 223, the average waveform calculator 224, the swing waveform calculator 225, and the waveform power calculator 226. For example, the second waveform estimator 23 processes the intermediate-cycle waveform in the same way as the above-discussed process, and thereby calculates an intermediate-cycle vibration component.

(Characteristics of Each Method)

Descriptions will be provided for a characteristic of each method. The characteristic for which descriptions are going to be provided are an effect of changes in the amplitude of the input waveform on the average waveform estimation. This is the case with all the short-, intermediate- and long-cycle average waveforms, and descriptions will be provided in which the first average waveform and the like are simply referred to as average waveforms.

FIG. 13 is a diagram for explaining a characteristic of the input waveform orientation of the method A. The characteristic of the input waveform orientation is that: the low-order polynomial expression model is conditioned to use the actual average waveform during the period time T1 and to pass through the average waveform at time T0; and thus, fluctuations may be inhibited during the period T2, and the shape of the average waveform during the period T2 is a smooth continuation of the shape of the average waveform during the period T1.

For example, as illustrated in (1) of FIG. 13, in a case where the amplitude of the input waveform increases after time T0, there is a tendency that because the input waveform-oriented method does not follow the increase in the amplitude, the input waveform-oriented method estimate an average waveform with a smaller amplitude from the extension tendency, and makes the estimated amplitude larger than the actual amplitude. Meanwhile, as illustrated in (2) of FIG. 13, in a case where the amplitude of the input waveform decreases after time T0, the input waveform-oriented method assumes that the original average waveform continues. For this reason, the divergence from the average waveform estimated based on the extension tendency is accordingly small, as well as the difference between the estimated amplitude and the actual amplitude is small.

Figure 14:
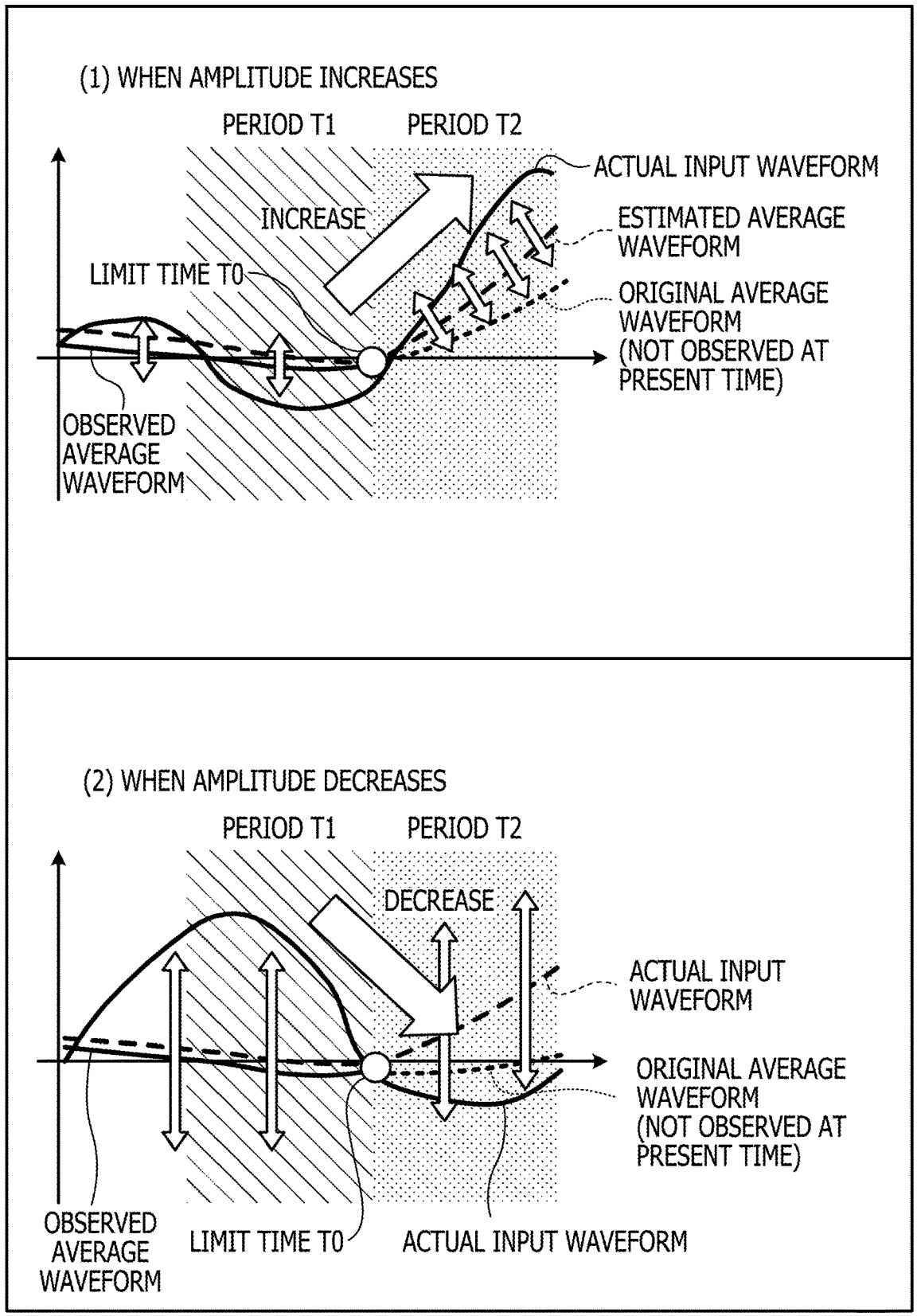
FIG. 14 is a diagram for explaining a characteristic of a prediction orientation of the method B.

FIG. 14 is a diagram for explaining a characteristic of the prediction orientation of the method B. The characteristic of the prediction-oriented method is as follows. The prediction-oriented method estimates an average waveform following a change in the input waveform on the assumption that the actual amplitude during the period T1 is maintained during the period T2 as well, and the estimated average waveform accordingly does not follow the change in the amplitude.

For example, as illustrated in (1) of FIG. 14, in a case where the amplitude of the input waveform increases after time T0, there is a tendency that because the prediction-oriented method estimates the average waveform on the assumption that the amplitude of the input waveform during the period T1 continues after time T0, the average waveform is excessively close to the input waveform, and the estimated amplitude is smaller than the actual amplitude. Meanwhile, as illustrated in (2) of FIG. 14, in a case where the amplitude of the input waveform decreases after time T0, there is a tendency that because the prediction-oriented method estimates the average waveform on the assumption that the amplitude of the input waveform during the period T1 continues after time T0, the average waveform becomes farther away from the input waveform whose amplitude is getting smaller, and the estimated amplitude is larger than the actual amplitude.

Figure 15:
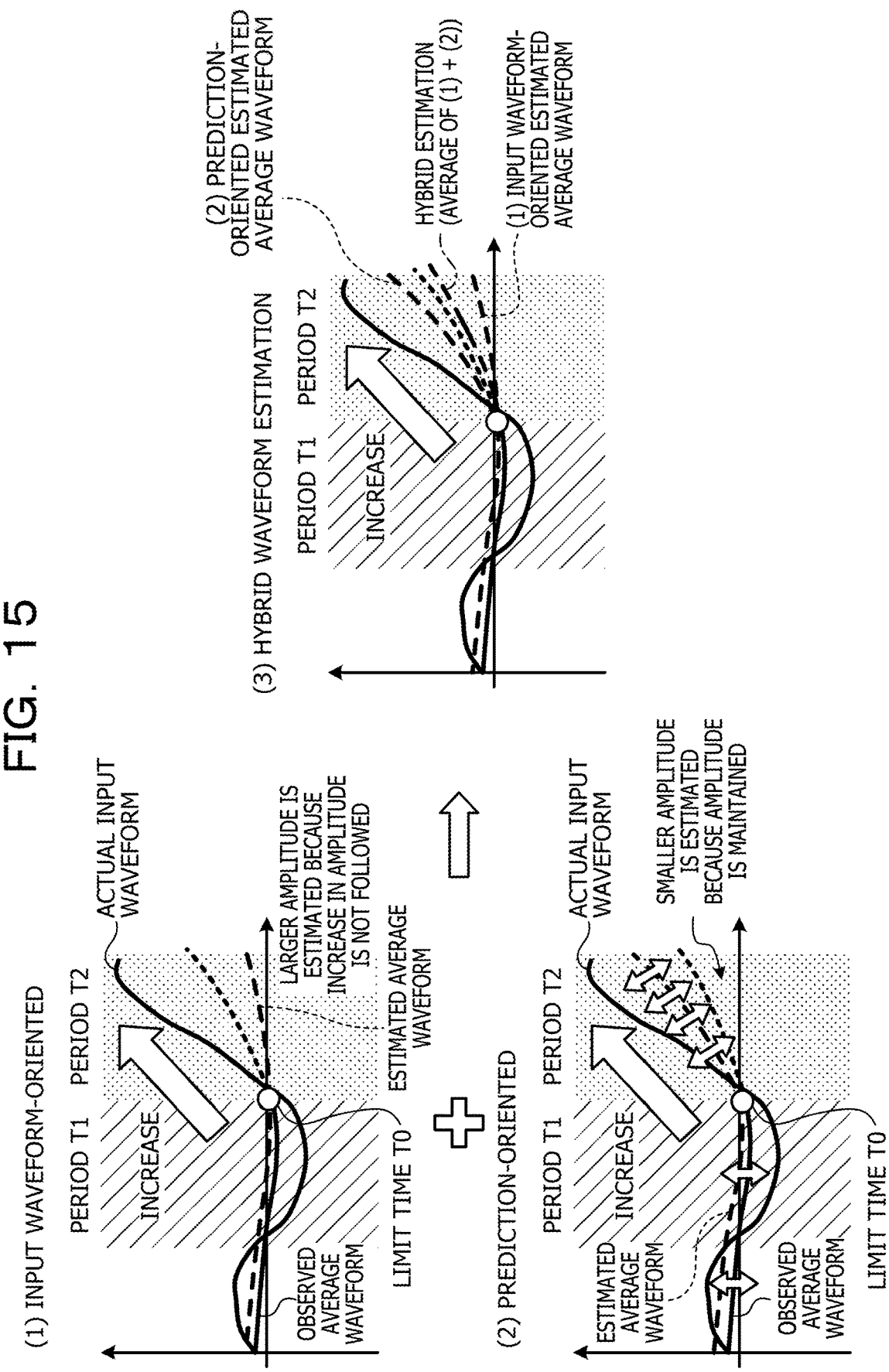
FIG. 15 is a diagram for explaining a characteristic of a hybrid waveform estimation in a case of an increase in amplitude.
Figure 16:
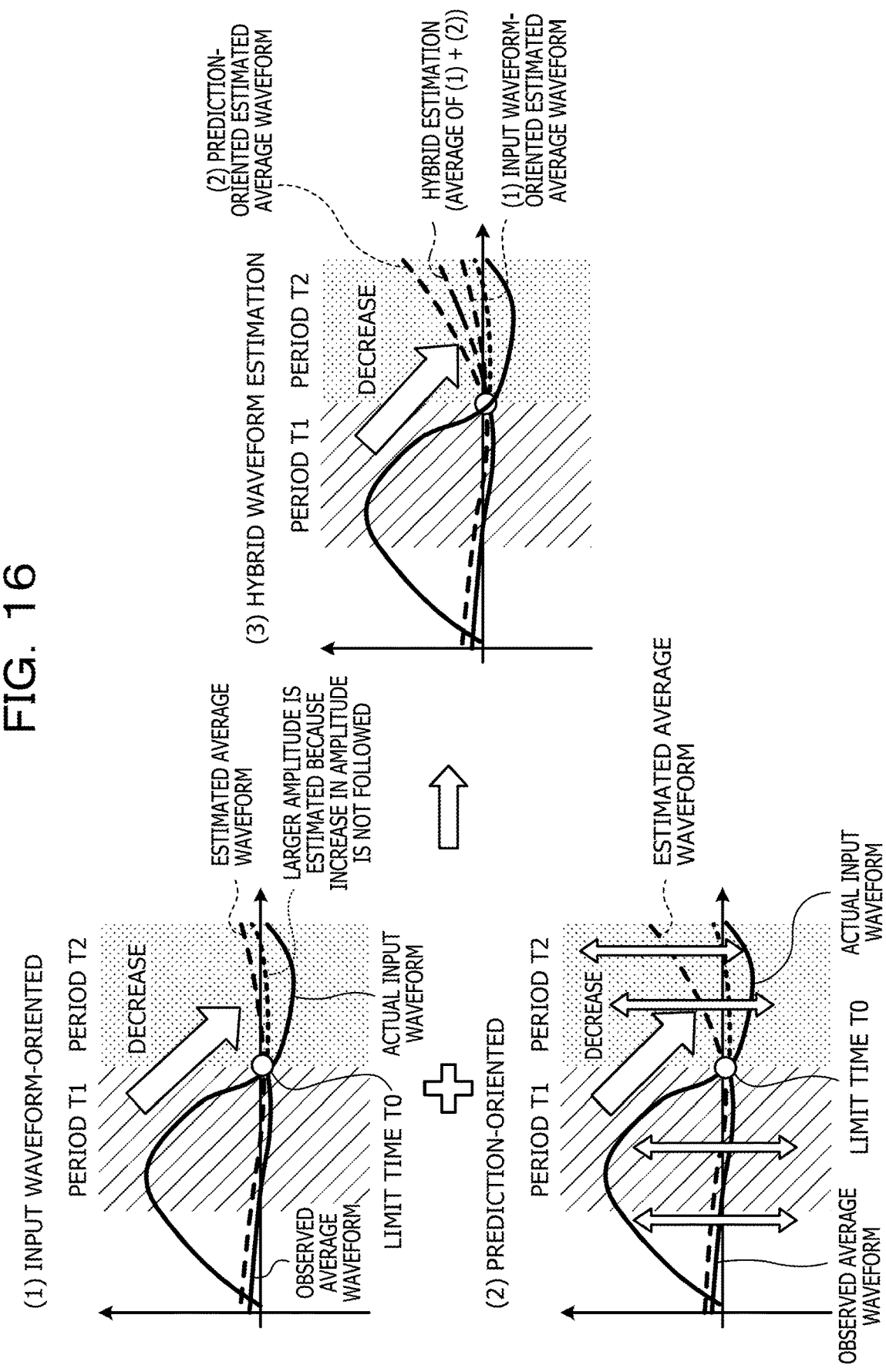
FIG. 16 is a diagram for explaining a characteristic of the hybrid waveform estimation in a case of a decrease in the amplitude.

As discussed above, the error tendency of the input waveform-oriented method is contrary to the error tendency of the prediction-oriented method. The sum of the two schemes makes the two error tendencies offset each other, and increases the accuracy of estimating the swing waveform. FIG. 15 is a diagram for explaining a characteristic of the hybrid waveform estimation in the case of an increase in the amplitude. FIG. 16 is a diagram for explaining a characteristic of the hybrid waveform estimation in the case of a decrease in the amplitude.

When the amplitude increases, as illustrated in (1) of FIG. 15, the input waveform-orientated method does not follow the increase in the amplitude, and estimates a larger amplitude. As illustrated in (2) of FIG. 15, the prediction-oriented method assumes the amplitude continues, and estimates a smaller amplitude. As illustrated in (3) of FIG. 15, the hybrid waveform estimation makes the mutually-contrary error tendencies of the two schemes offset each other even when the amplitude increases, and accordingly increase the accuracy of estimating the average waveform.

When the amplitude decreases, as illustrated in (1) of FIG. 16, the input waveform-orientated method makes the difference between the estimated amplitude and the actual amplitude small. As illustrated in (2) of FIG. 16, the prediction-oriented method estimates a larger amplitude than the actual amplitude. As illustrated in (3) of FIG. 16, the hybrid waveform estimation makes the difference between the errors of the two schemes small, and accordingly increases the accuracy of estimating the average waveform.

(Simulation Result of Each Method in Case of Increase in Amplitude)

Figure 17:
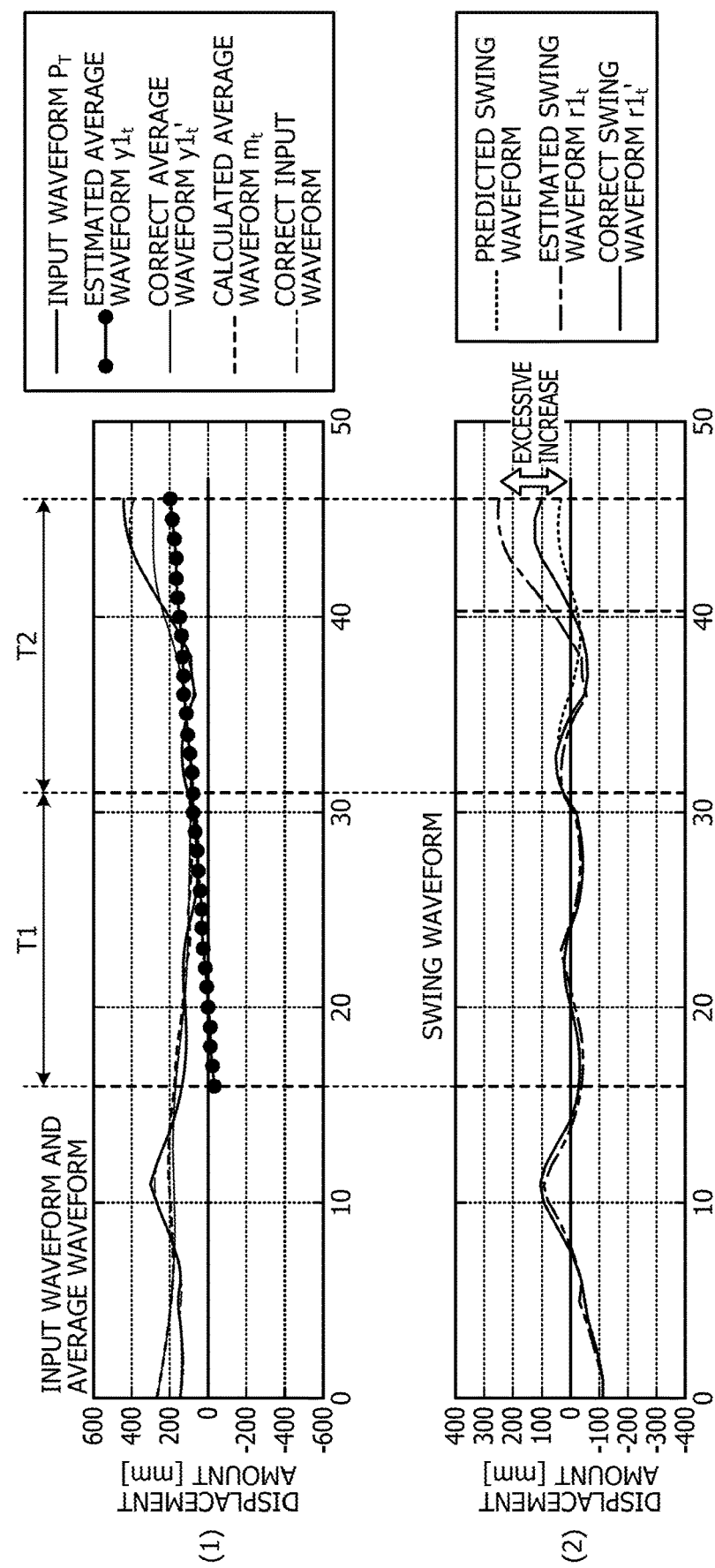
FIG. 17 is a diagram for explaining a simulation result of the method A (in the case of the increase in the amplitude)
Figure 18:
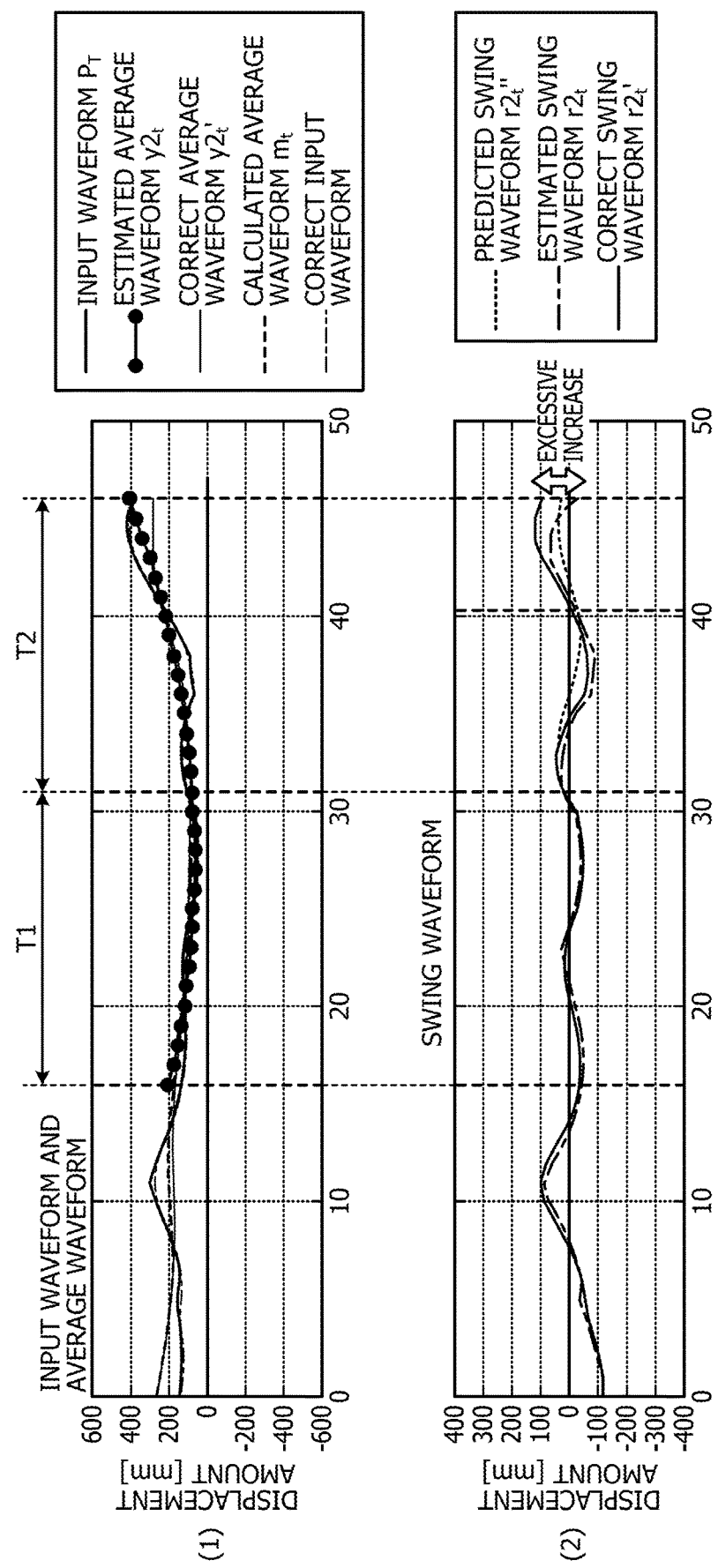
FIG. 18 is a diagram for explaining a simulation result of the method B (in the case of the increase in the amplitude)
Figure 19:
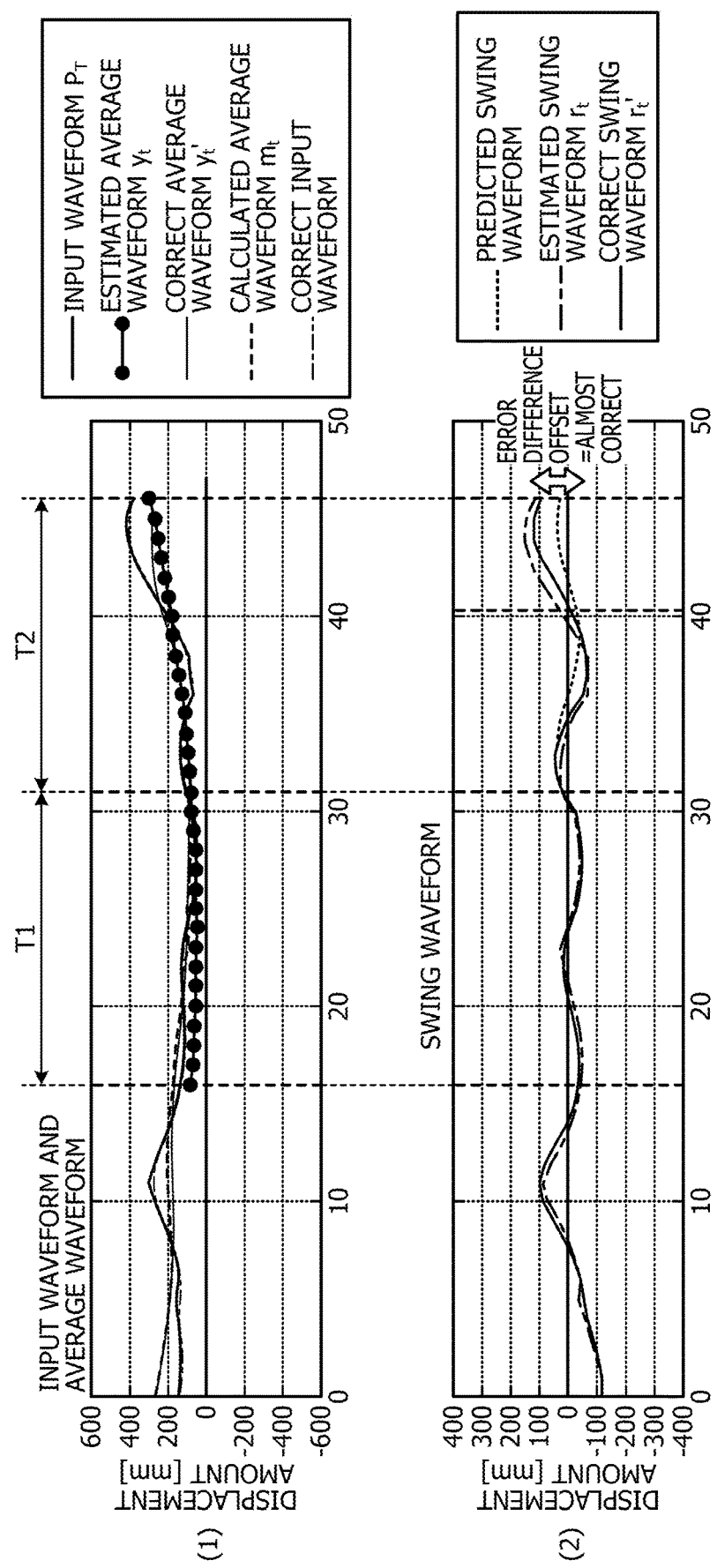
FIG. 19 is a diagram for explaining a simulation result of the hybrid waveform estimation (in the case of the increase in the amplitude)

FIG. 17 is a diagram for explaining a simulation result of the method A (in the case of an increase in the amplitude). FIG. 18 is a diagram for explaining a simulation result of the method B (in the case of the increase in the amplitude). FIG. 19 is a diagram for explaining a simulation result of the hybrid waveform estimation (in the case of the increase in the amplitude).

FIG. 17 illustrates a result of estimation by the method A in which the first average waveform $y1_t$ during the period T2 is estimated using the first average waveform $m_t$ calculated by the past waveform calculator 221, and a result of estimation by the method A in which the first swing waveform $r_t$ during the period T2 is estimated using the estimated first average waveform $y1_t$ during the period T2. As illustrated in (1) of FIG. 17, when the amplitude of the input waveform $p_t$ increases over the time from the period T1 through the period T2, an error difference between the estimated average waveform $y1_t$ during the period T2 and a correct average waveform $y1_t'$ during the period T2 which is obtained from the simulation is large. Accordingly, as illustrated in (2) of FIG. 17, the amplitude of the estimated first swing waveform $r1_t$ during the period T2 is larger than the amplitude of the correct swing waveform $r1_t'$ during the period T2 which is obtained from the simulation (an excessive increase).

FIG. 18 illustrates a result of estimation by the method B in which the first average waveform $y2_t$ during the period T2 is estimated using the first average waveform $m_t$ and a second swing waveform $r2_t''$ which are calculated by the past waveform calculator 221, and a result of estimation by the method B in which the first swing waveform $r2_t$ during the period T2 is estimated using the estimated first average waveform $y2_t$ during the period T2. As illustrated in (1) of FIG. 18, when the amplitude of the input waveform $p_t$ increases over the time from the period T1 through the period T2, an error difference between the estimated average waveform $y2_t$ during the period T2 and a correct average waveform $y2_t'$ during the period T2 which is obtained from the simulation is large. Accordingly, as illustrated in (2) of FIG. 18, the amplitude of the estimated first swing waveform $r2_t$ during the period T2 is smaller than the amplitude of a correct swing waveform $r2_t'$ during the period T2 which is obtained from the simulation (an excessive decrease).

FIG. 19 is a diagram illustrating a summation of the first average waveform obtained in (1)(2) of FIG. 17 and the first average waveform obtained in (1)(2) of FIG. 18. As illustrated in (1) of FIG. 19, the hybrid waveform estimation sums up the first average waveform $y1_t$ obtained in (1) of FIG. 17 using the method A and the first average waveform $y2_t$ obtained in (1) of FIG. 18 using the method B, and estimates the first average waveform $y_t$ which is close to an intermediate value between the first average waveform $y1_t$ obtained using the method A and the first average waveform $y2_t$ obtained using the method B. Accordingly, as illustrated in (2) of FIG. 19, the hybrid waveform estimation makes the error differences of the respective methods A, B offset each other, and thus makes smaller the error difference between the amplitude of the estimated first swing waveform $r_t$ during the period T2 and the amplitude of the correct swing waveform $r1_t'$ during the period T2 which is obtained from the simulation.

(Simulation Result of Each Method in Case of Decrease in Amplitude)

Figure 20:
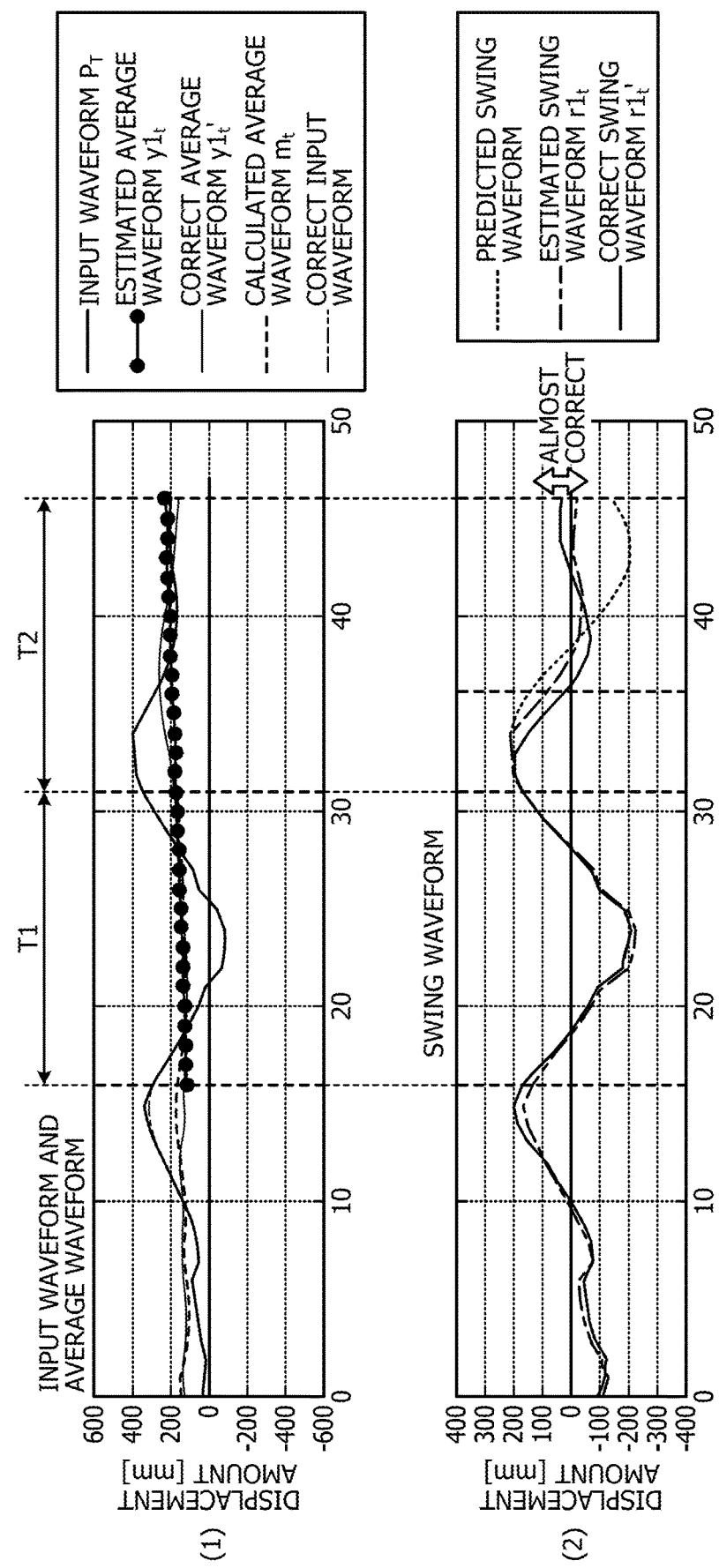
FIG. 20 is a diagram for explaining a simulation result of the method A (in the case of the increase in the amplitude)
Figure 21:
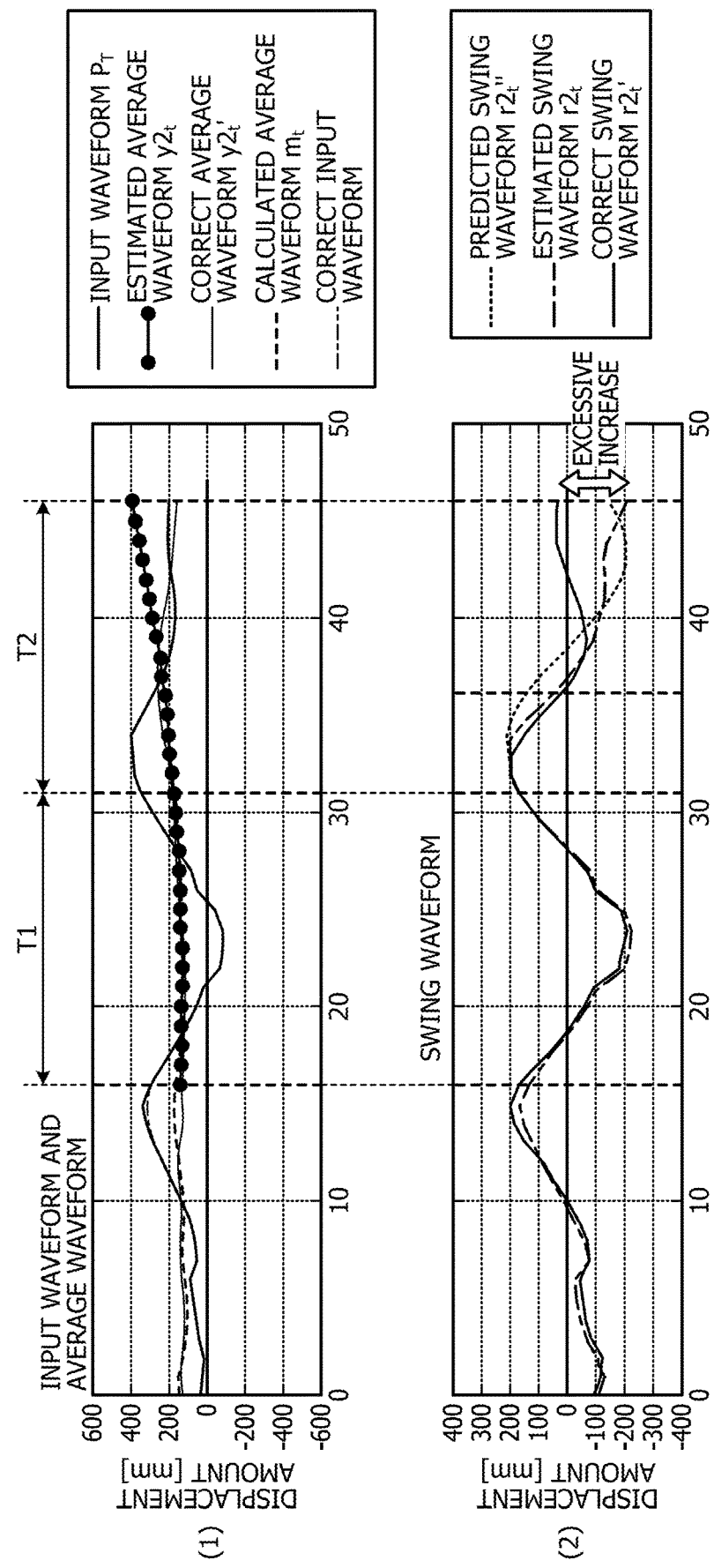
FIG. 21 is a diagram for explaining a simulation result of the method B (in the case of the increase in the amplitude)
Figure 22:
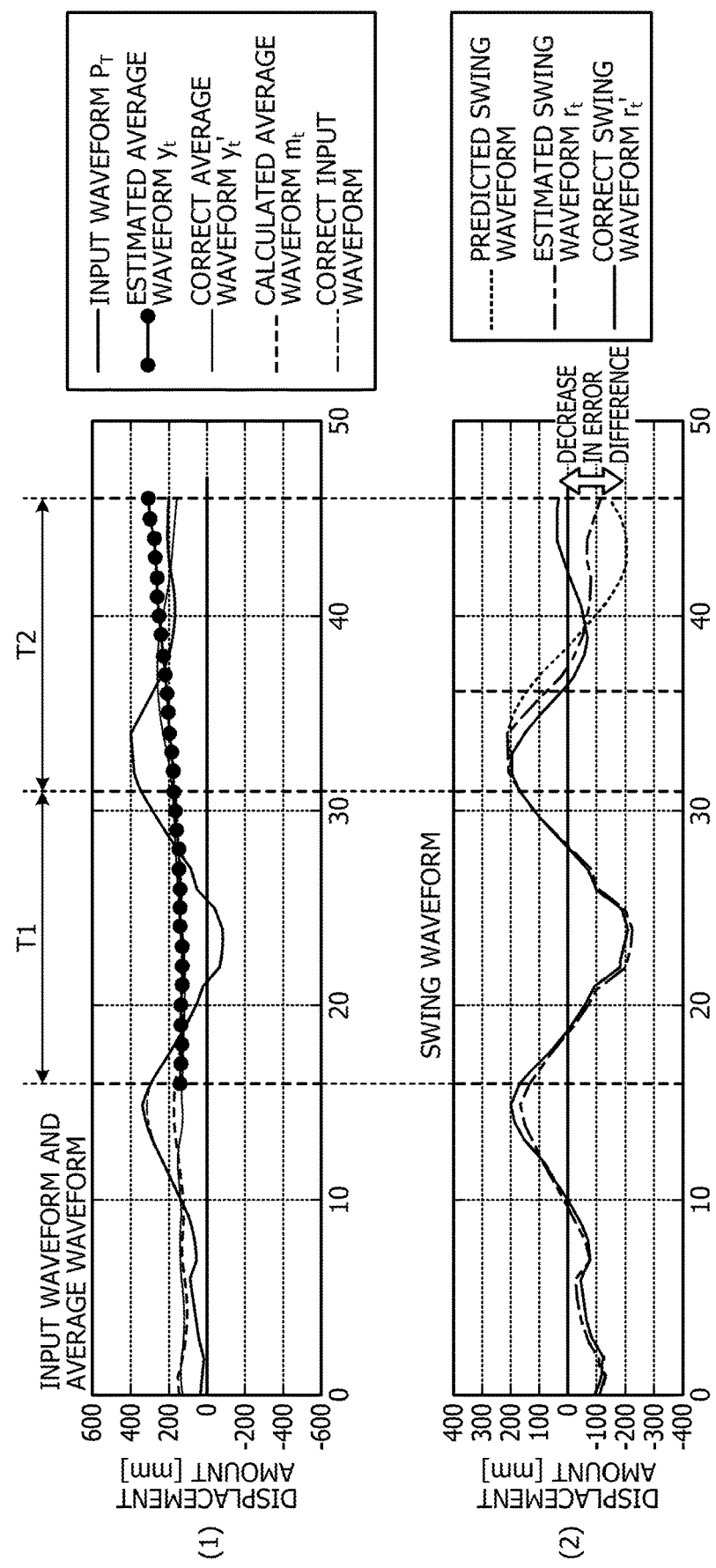
FIG. 22 is a diagram for explaining a simulation result of the hybrid waveform estimation (in the case of the increase in the amplitude)

FIG. 20 is a diagram for explaining a simulation result of the method A (in the case of a decrease in the amplitude). FIG. 21 is a diagram for explaining a simulation result of the method B (in the case of the decrease in the amplitude). FIG. 22 is a diagram for explaining a simulation result of the hybrid waveform estimation (in the case of the decrease in the amplitude).

FIG. 20 illustrates a result of estimation by the method A in which the first average waveform $y1_t$ during the period T2 is estimated using the first average waveform $m_t$ calculated by the past waveform calculator 221, and a result of estimation by the method A in which the first swing waveform $r1_t$ during the period T2 is estimated using the estimated first average waveform $y1_t$ during the period T2. As illustrated in (1) of FIG. 20, when the amplitude of the input waveform $p_t$ decreases over the time from the period T1 through the period T2, an error difference between the estimated average waveform $y1_t$ during the period T2 and a correct average waveform $y1_t'$ during the period T2 which is obtained from the simulation is small. Accordingly, as illustrated in (2) of FIG. 20, the amplitude of the estimated first swing waveform $r1_t$ during the period T2 is very similar to the amplitude of the correct swing waveform $r1_t'$ during the period T2 which is obtained from the simulation.

FIG. 21 illustrates a result of estimation by the method B in which the first average waveform $y2_t$ during the period T2 is estimated using the first average waveform $m_t$ and a second swing waveform $r2_t''$ which are calculated by the past waveform calculator 221, and a result of estimation by the method B in which the first swing waveform $r2_t$ during the period T2 is estimated using the estimated first average waveform $y2_t$ during the period T2. As illustrated in (1) of FIG. 21, when the amplitude of the input waveform $p_t$ decreases over the time from the period T1 through the period T2, an error difference between the estimated average waveform $y2_t$ during the period T2 and a correct average waveform $y2'$ during the period T2 which is obtained from the simulation is large. Accordingly, as illustrated in (2) of FIG. 21, the amplitude of the estimated first swing waveform $r2_t$ during the period T2 is larger than the amplitude of a correct swing waveform $r2'$ during the period T2 which is obtained from the simulation (an excessive increase).

FIG. 22 is a diagram illustrating a summation of the first average waveform obtained in (1)(2) of FIG. 20 and the first average waveform obtained in (1)(2) of FIG. 21. As illustrated in (1) of FIG. 22, the hybrid waveform estimation sums up the first average waveform $y1_t$ obtained in (1) of FIG. 20 using the method A and the first average waveform $y2_t$ obtained in (1) of FIG. 21 using the method B, and estimates the first average waveform $y_t$ which is close to an intermediate value between the first average waveform $y1_t$ obtained using the method A and the first average waveform $y2_t$ obtained using the method B. Accordingly, as illustrated in (2) of FIG. 22, the hybrid waveform estimation reduces the error difference of the method B using the error difference of the method A, and thus makes the error difference between the amplitude of the estimated first swing waveform $r_t$ during the period T2 and the amplitude of the correct swing waveform r1$_t'$ during the period T2 which is obtained from the simulation become smaller than the error difference of the method B.

As discussed above, the use of both the method A and method B makes it possible to combine the method B good at the steady-state characteristic with the method A which exhibits the opposite characteristic when faced with increase and decrease changes, and to realize the swing waveform estimation good at following the increase and decrease.

(Simulation Result of Waveform Power)

Figure 23:
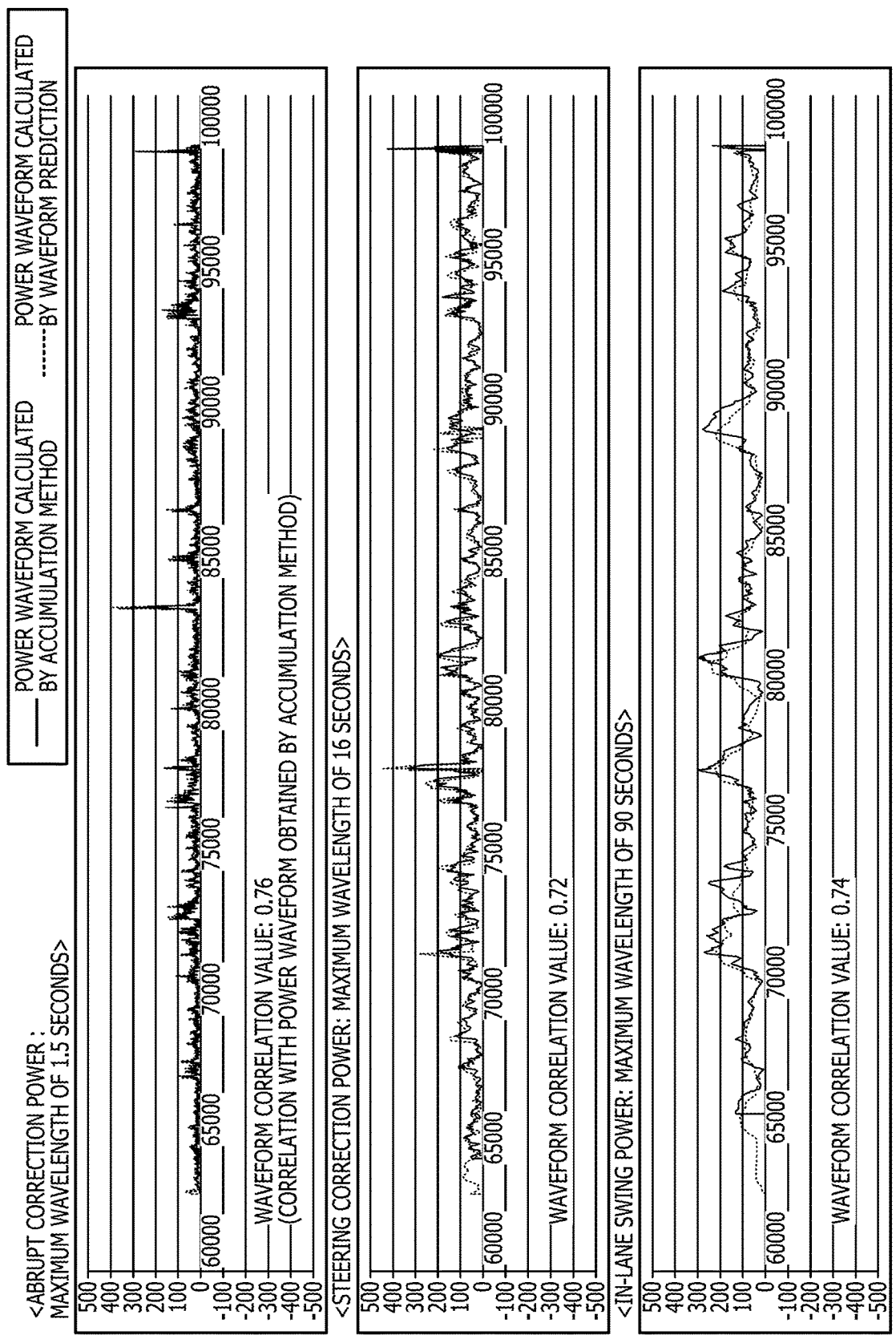
FIG. 23 is a diagram for explaining a simulation result of waveform power estimation by the hybrid waveform estimation method.

For each of the short-, intermediate- and long-cycle component waveforms from the start of the run until the present time, descriptions will be provided for a simulation result of a finally-estimated waveform power. FIG. 23 is a diagram for explaining a simulation result of waveform power estimation by the hybrid waveform estimation method.

For each of the short-, intermediate- and long-cycle component waveforms respectively with maximum wavelengths of approximately 1.5 seconds, 16 seconds and 90 seconds, FIG. 23 illustrates a correlation (waveform correlation value) between a waveform power obtained by the above-discussed hybrid waveform estimation according to Embodiment 1 and a waveform power obtained by an accumulation method which is capable of precisely performing a drive determination process although not in real time. As illustrated in FIG. 23, each waveform power has a high correlation between a waveform estimated from the waveform power and a waveform obtained by the accumulation method, no matter how long the cycle is. From this, it is confirmed that the hybrid waveform estimation is capable of making the prediction accurately enough for the dangerous faltering analysis.

Figure 24:
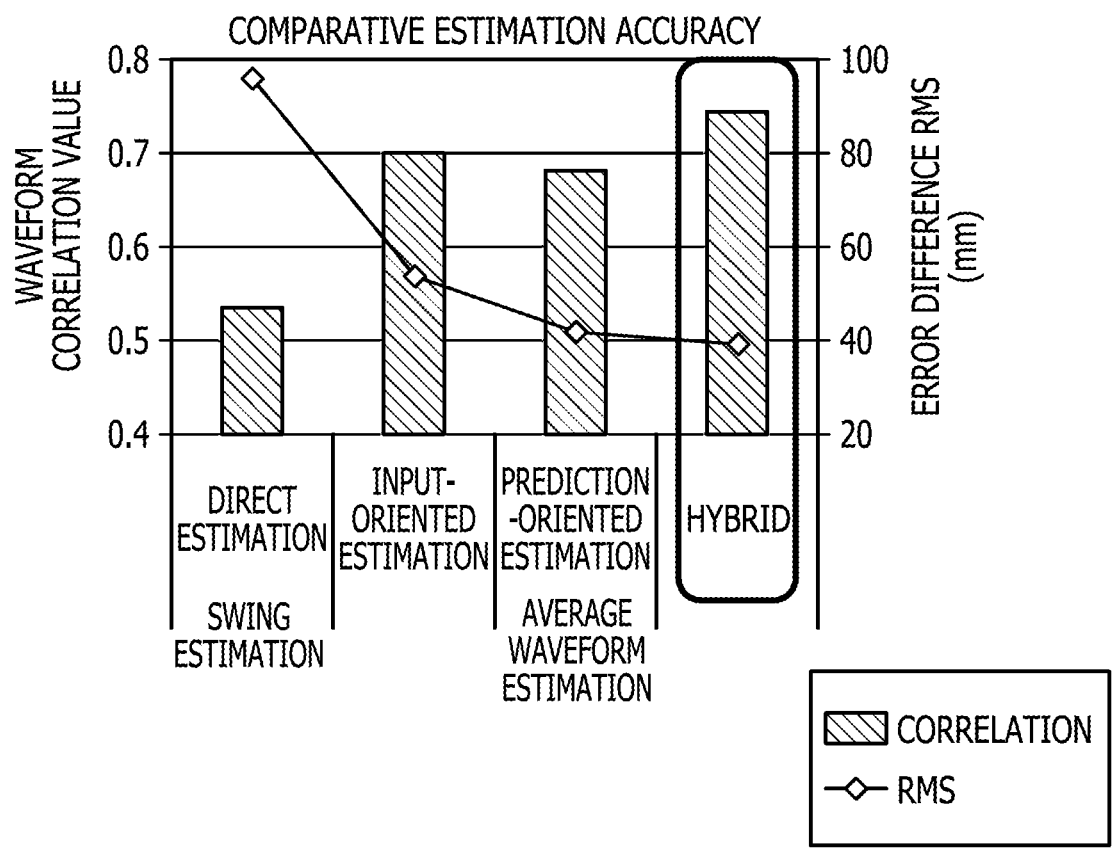
FIG. 24 is a diagram for explaining a simulation result of waveform power estimation by each method.

FIG. 24 is a diagram for explaining a simulation result of waveform power estimation by each method. For each of a method of directly estimating the swing waveform, the input waveform-oriented method A, the prediction-oriented method B, and the hybrid waveform estimation method, FIG. 24 illustrates a correlation, and a RMS error difference, between the waveform of a finally-estimated waveform power and the waveform of a waveform power obtained by the accumulation method. As illustrated in FIG. 24, a correlation between the hybrid waveform estimation and the accumulation method is the highest, and the RMS error difference obtained from the hybrid waveform estimation is the smallest. From FIG. 24, it is confirmed that the hybrid waveform estimation method makes the accuracy of the dangerous faltering analysis higher than any other method.

(Functional Block of Danger Determination Unit)

Figure 25:
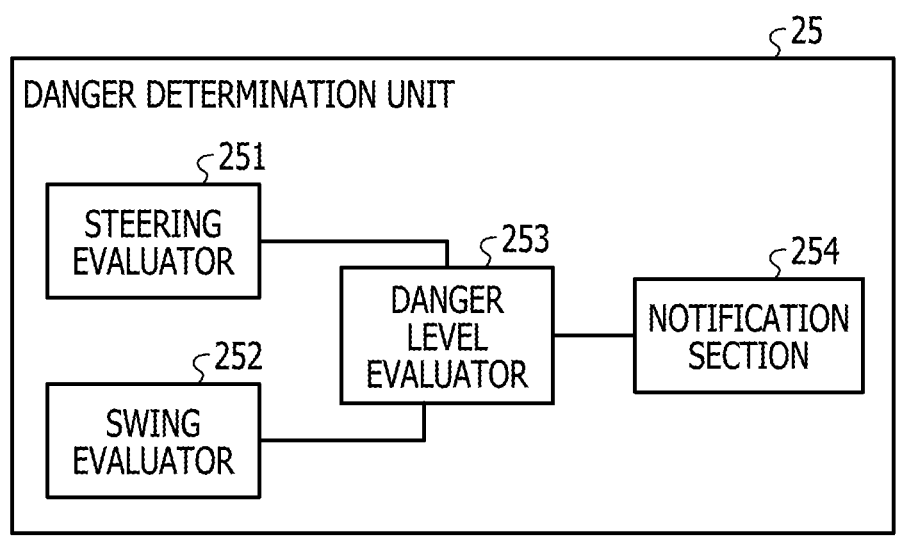
FIG. 25 is a functional block diagram illustrating a functional configuration of a danger determination unit.

FIG. 25 is a functional block diagram illustrating a functional configuration of the danger determination unit 25. The danger determination unit 25 is an example of a determination unit which determines how dangerously the vehicle is being driven, for example, based on the characteristic amount of each of the short-, intermediate- and long-cycle vibration components. The danger determination unit 25 includes a steering evaluator 251, a swing evaluator 252, a danger level evaluator 253, and a notification section 254.

The steering evaluator 251 is a processor which is related to the drive steering of the driver, and which evaluates the driving operation based on what condition makes the driver turn the steering wheel abruptly. The steering evaluator 251 obtains a waveform power with a short cycle Ts from the first waveform estimator 22. The steering evaluator 251 further obtains a waveform value (amplitude value) representing an intermediate-cycle vibration component. Thereafter, the steering evaluator 251 calculates an abrupt steering score value based on the obtained waveform power and waveform value, and outputs the calculated abrupt steering score value to the danger level evaluator 253.

For example, the steering evaluator 251 calculates the abrupt steering waveform power score value s1 using an evaluation function expressed with $$f1(x)=\alpha 1x+\beta 1 \quad (20\text{-}1)$$

where $\alpha 1$ and $\beta 1$ are constants which are set depending on types of waveform power to be converted into a score value, or $$f1(x)=(\tan h(x/2)+1)/2 \quad (20\text{-}2)$$

For example, when the waveform power with a short cycle of Ts is p1, the steering evaluator 251 calculates s1=f1(p1). The evaluation function f1(x) is a function expressed with Equation 20-1 which obtains the score value from the waveform power by linear transformation, or a function expressed with Equation 20-2 which obtains the score value from the waveform power by nonlinear transformation.

The steering evaluator 251 calculates a normal steering swing rate expressed with $$tv=\text{MIN}(|W2|/\text{base},1) \quad (21)$$

where w2 is a waveform value (normal steering swing waveform value) of the intermediate-cycle vibration component, and base is a threshold distance. For example, as learned from Equation 21, the steering evaluator 251 selects the smaller one from a lower limit value and a value obtained by dividing the absolute value of the waveform value w2 by the threshold distance base, and uses the selected value as the normal steering swing rate tv. The threshold distance base is a preset value, and is 200 mm, for example. In Equation 21, the lower limit value is set at "1". Thereafter, the steering evaluator 251 multiplies the abrupt steering waveform power score value s1 by the normal steering swing rate tv, and thereby calculates an abrupt steering score value sc1=s1*tv.

The swing evaluator 252 is a processor which is related to the drive steering of the driver, and which evaluates how large the overall swing of the running trace is. The swing evaluator 252 calculates an overall swing score value based on the intermediate- and long-cycle waveform powers obtained from the second and third waveform evaluators 23, 24, and outputs the calculated overall swing score value to the danger level evaluator 253.

For example, to begin with, using the evaluation function f1(x), the swing evaluator 252 calculates a normal steering waveform power score value S2 and an in-lane swing waveform power score value S3. For example, when an intermediate-cycle waveform power is p2 and a long-cycle waveform power is p3, the swing evaluator 252 calculates S2=f1(p2) and S3=f1(p3). Thereafter, the swing evaluator 252 calculates a power score increase rate g using $$g=((2\sqrt{S2\cdot S3})/(S2+S3))^2 \quad (22)$$

Subsequently, the swing evaluator 252 multiplies the sum of the normal steering waveform power score value S2 and the in-lane swing waveform power score value S3 by the power score increase rate g, and thereby calculates an overall swing score value sc2=(S2+S3)*g.

The danger level evaluator 253 is a processor which evaluates how dangerously the driver drives the vehicle based on the evaluation result from the steering evaluator 251 and the evaluation result from the swing evaluator 252.

To begin with, the danger level evaluator 253 obtains a lateral displacement m1 of the running vehicle from the running trace. Thereafter, the danger level evaluator 253 calculates a lateral displacement danger score value cr using an evaluation function expressed with $$f2(x)=f1(x) \quad (23\text{-}1)$$

or $$f2(x)=\alpha 2x+\beta 2 \quad (23\text{-}2)$$

where α2 and β2 are constants. For example, the danger level evaluator 253 calculates cr=f2(m1). In the case of nonlinear transformation, the evaluation function f2(x) is a function which is the same as the evaluation function f1(x), as learned from Equation 23-1. In the case of linear transformation, the evaluation function f2(x) is a linear function expressed with Equation 23-2.

Thereafter, the danger level evaluator 253 multiplies the sum of the abrupt steering score value sc1 and the overall swing score value sc2 by the lateral displacement danger score value cr, and thereby calculates a danger level score value sc3=(sc1+sc2)*cr.

Subsequently, the danger level evaluator 253 outputs the calculated danger level score value sc3 to the notification section 254. The danger level evaluator 253 associates together the time length of the running trace and the danger level score value sc3 both having been used for the danger determination, and stores them onto the evaluation value DB 15. In addition to the danger level score value sc3, the abrupt steering score value sc1 and the overall swing score value sc2 may be stored onto the evaluation value DB 15.

The notification section 254 is a processor which determines that the danger level is high when the danger level score value sc3 exceeds a certain value, and notifies the danger determination to the automatic drive controller 2. For example, in the case where the danger level score value sc3 obtained from the danger level evaluator 253 exceeds the certain value, the notification section 254 notifies to the automatic drive controller 2 that a dangerous faltering occurs. Upon receipt of the notice from the notification section 254, the automatic drive controller 2 switches the vehicle drive mode to the automatic drive mode. The notification section 254 may be configured to notify the danger to the driver by displaying a message about the occurrence of the dangerous faltering on a display or the like, or by issuing a voice message about the occurrence of the dangerous faltering.

(Process Flows)

Process flows will be described. Descriptions will be provided for an overall process flow, waveform estimation process flows, and a danger determination process flow.

(Overall Process Flow)

Figure 26:
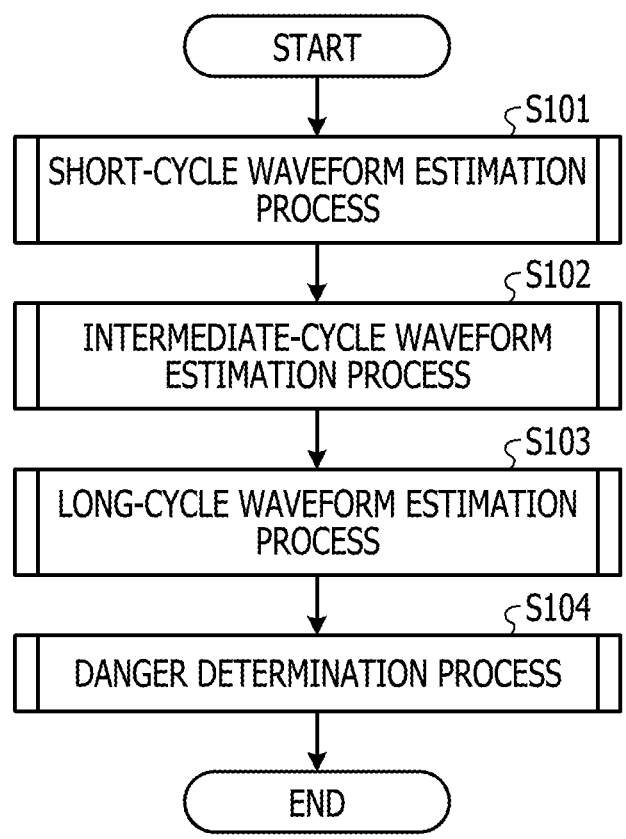
FIG. 26 is a flowchart illustrating an overall process flow.

FIG. 26 is a flowchart illustrating the overall process flow. As illustrated in FIG. 26, the first waveform estimator 22 performs a short-cycle waveform estimation process (S101); the second waveform estimator 23 performs an intermediate-cycle waveform estimation process (S102); subsequently, the third waveform estimator 24 performs a long-cycle waveform estimation process (S103); and thereafter, the danger determination unit 25 performs a danger determination process (S104), and terminates the process.

(Waveform Estimation Process Flows)

Figure 27:
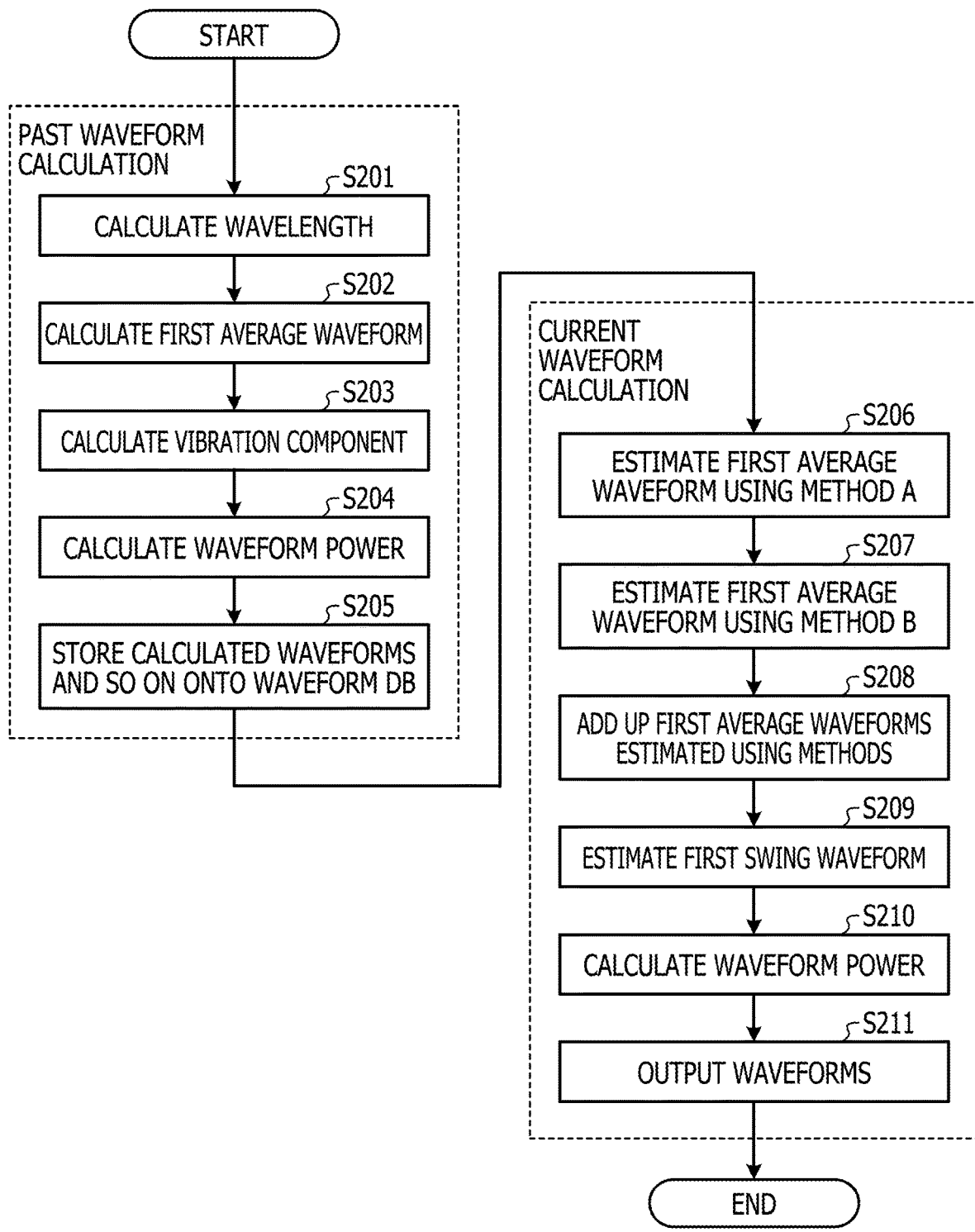
FIG. 27 is a flowchart illustrating a waveform estimation process flow.

FIG. 27 is a flowchart illustrating a waveform estimation process flow. Descriptions will be hereinbelow provided for the short-cycle waveform estimation process to be performed by the first waveform estimator 22. The waveform estimation processes to be performed by the second and third waveform estimators 23, 24 are similar to the short-cycle waveform estimation process, and description will be omitted.

As illustrated in FIG. 27, the first waveform estimator 22 perform a past waveform calculation. For example, the past waveform calculator 221 calculates a wavelength (S201), calculates a first average waveform (S202), and calculates a vibration component (S203). Subsequently, the past waveform calculator 221 calculates a waveform power (S204), and stores the calculated waveforms and the like onto the waveform DB 13 and the like (S205).

Thereafter, the past waveform calculator 221 performs a current waveform calculation. For example, the swing waveform estimator 222 or the average waveform estimator 223 estimates a first average waveform using the method A (S206), and estimates a first average waveform using the method B (S207).

Subsequently, the average waveform calculator 224 adds up the first average waveforms which are estimated using the respective methods (S208). After that, the swing waveform calculator 225 estimates a first swing waveform from the added-up first average waveforms and the input waveform (S209).

Thereafter, the waveform power calculator 226 calculates the waveform power of the first swing waveform (vibration component) which is calculated in step S209 (S210). After that, the first waveform estimator 22 outputs the waveforms the like to the subsequent processor (S211), and terminates the process.

(Danger Determination Process Flow)

Figure 28:
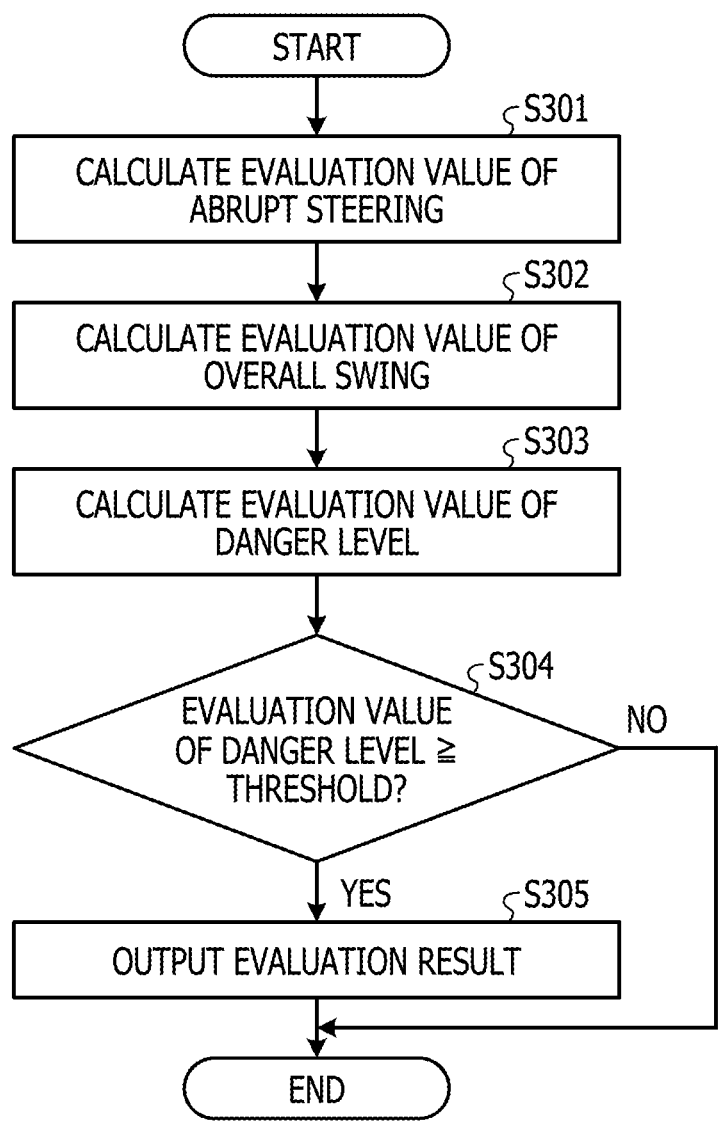
FIG. 28 is a flowchart illustrating a danger determination process flow.

FIG. 28 is a flowchart illustrating the danger determination process flow. As illustrated in FIG. 28, the steering evaluator 251 calculates an evaluation value (abrupt steering score value sc1) of an abrupt steering (S301). Subsequently, the swing evaluator 252 calculates an evaluation value (overall swing score value sc2) of an overall swing (S302). Thereafter, the danger level evaluator 253 calculates an evaluation value (danger level score value sc3) of a danger level based on the evaluation value of the abrupt steering which is calculated in step S301, and the evaluation value of the overall swing which is calculated in step S302 (step S303). Thereafter, if the evaluation value of the danger level is equal to or greater than a threshold (if Yes) (S304), the notification section 254 outputs the evaluation result to the automatic drive controller 2 (S305). If the evaluation value is less than the threshold (if No) (S304), the notification section 254 terminates the process.

(Effects)

As discussed above, the on-board device 10 according to Embodiment 1 estimates the first vibration component at the present time using: the input waveform based on the running trace of the vehicle which is running in a roadway; and the calculated first vibration component (parallel waveform) which is calculated from the input waveform, and which is less than a first frequency. The on-board device 10 estimates the first vibration component at the present time using: the input waveform; the calculated first vibration component; and the second vibration component at the present time estimated from the calculated second vibration component (swing waveform) which is calculated from the input waveform, and which is equal to or greater than the first frequency. Based on the estimated first vibration components, the on-board device 10 calculates the second vibration component at the present time from the input waveform.

That is to say, the on-board device 10 according to Embodiment 1 pays attention to the waveform decomposition method related to the steering action. The on-board device 10 estimates the average waveform which corresponds to the direct-current component, and which changes gently and is stably estimated using the low-order parameters, using the input waveform observed during the immediately-preceding half wavelength, and the estimated swing waveform estimated from the swing waveform during the immediately-preceding half wavelength, as restrictions. Thereafter, the on-board device 10 calculates the swing waveform by the arithmetic operation of subtracting "the average waveform" from "the input waveform". Thereby, the on-board device 10 is capable of estimating the waveform power at the present time with high accuracy.

Thus, the on-board device 10 according to Embodiment 1 is capable of estimating in real time whether the running state at the present time is a dangerous faltering. The on-board device 10 according to Embodiment 1 is capable of: determining the running state in real time from the in-lane running trace which is obtained based on the white-line detection technique using an on-board system such as a drive recorder; and feeding back to the driver.

Embodiment 2

Although the foregoing descriptions have been provided for the embodiment according the present disclosure, the present disclosure may be carried out as various different modes instead of the above-discussed embodiment.

(Determination Method)

The above-discussed calculation of the evaluation values by the danger determination unit 25 is not limited to the specifically-described calculation example. For example, the danger determination unit 25 may be configured to calculate the evaluation values from the short-cycle vibration component using a phase of the in-lane swing or the like.

For example, the steering evaluator 251 of the danger determination unit 25 illustrated in FIG. 25 may be configured to detect and evaluate an abrupt steering of the driver using the lateral displacement of the vehicle, the phase of the in-lane swing, and the waveform power of the vibration component rt with a short cycle Ts.

For example, the steering evaluator 251 obtains a lateral displacement of the running vehicle from the running trace. The steering evaluator 251 further calculates a phase of the in-lane swing from the short-cycle vibration component. That is to say, the steering evaluator 251 calculates the phase (change denoted by reference sign d in FIG. 2) of the in-lane swing which represents timing at which the driver manipulates the steering wheel (turns the steering wheel) from a long-term perspective. Since the calculated phase represents the timing at which the driver manipulates the steering wheel, roadside ends (swing ends) indicated by white solid and dashed lines suggest how highly dangerous the steering is. The steering evaluator 251 may calculate the phase using various publicly-known methods.

Figure 29:
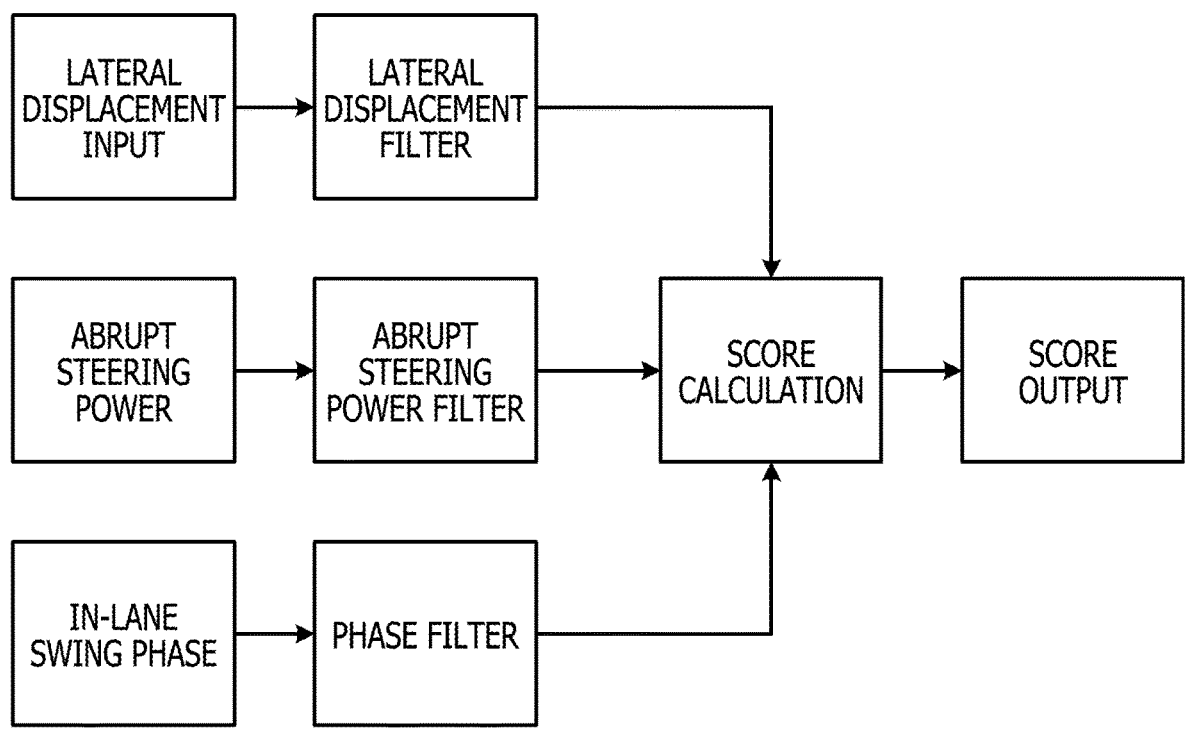
FIG. 29 is a diagram for explaining a process to be performed by a steering evaluator.

FIG. 29 is a diagram for explaining a process to be performed by the steering evaluator 251. As illustrated in FIG. 29, the steering evaluator 251 calculates a normalized value by filtering the lateral displacement. Similarly, the steering evaluator 251 filters and thereby normalizes the short-cycle waveform power (abrupt steering power), and phase-filters and normalizes the phase of the in-lane swing. Thereafter, the steering evaluator 251 calculates a score value of the abrupt steering by adding up the normalized values, and outputs the score value to the danger level evaluator 253.

Figure 30:
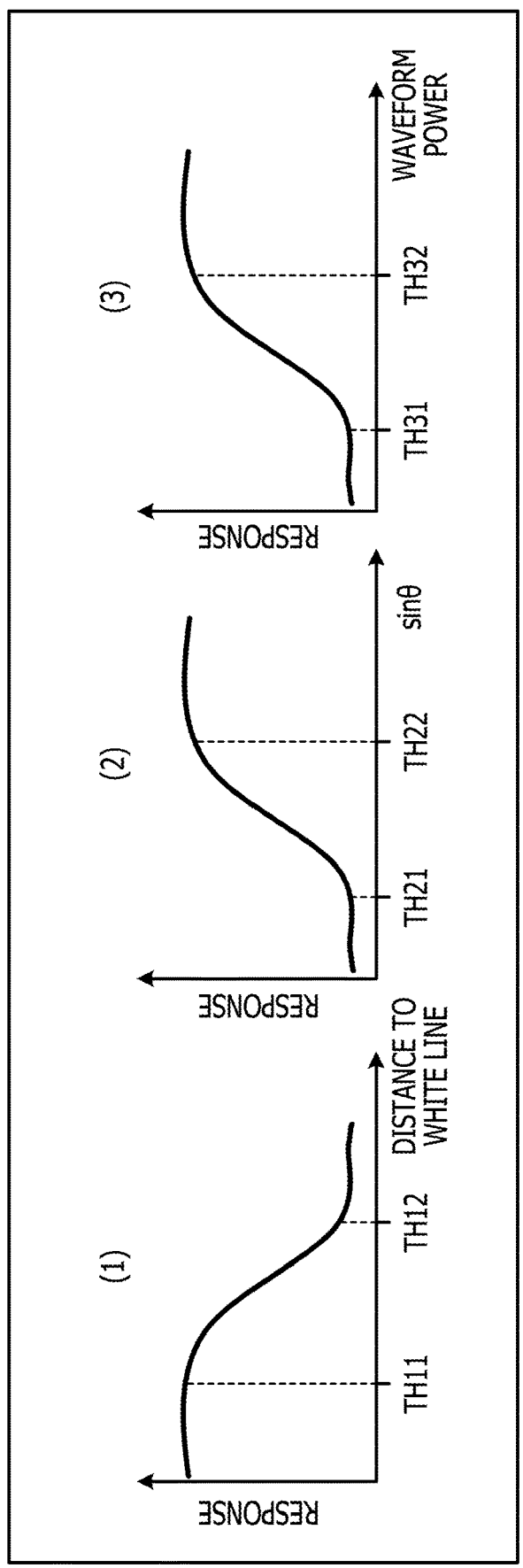
FIG. 30 is a diagram for explaining filters to be used for an abrupt steering evaluation.

Descriptions will be provided for filters to be used by the steering evaluator 251. FIG. 30 is a diagram for explaining filters to be used for the abrupt steering evaluation. The filters illustrated in FIG. 30 are saturation filters, that is to say, filters whose outputs saturate at large and small values. The filter illustrated in Part (1) of FIG. 30 is a filter which is applied to the amount of lateral displacement, and which obtains a response value depending on the distance of the left or right which is closer to the white lane. This filter obtains a higher response value as the distance from the white line becomes shorter. For example, as the distance from the white line (white line distance) becomes longer beyond a near distance (TH11), the response value becomes smaller. Once the white line distance exceeds a threshold TH12, the response value converges to a certain value.

The filter illustrated in Part (2) of FIG. 30 is a filter which is applied to the phase of the in-lane swing. This filter calculates sin θ from the phase θ of the in-lane swing, and outputs a high response value while the phase is at the wave end. For example, the response value becomes gradually larger after the phase exceeds a threshold TH21 of the wave end, and converges to a certain value after the phase exceeds a threshold TH22.

The filter illustrated in Part (3) of FIG. 30 is a filter which is applied to the abrupt steering power, and which responds strongly when the abrupt steering power exceeds a threshold TH31. For example, this filter returns a value close to a response maximum value at a threshold TH32 where the power is larger than at a threshold TH31. The thresholds TH11 to TH32 are set at the respective individual values in advance.

Figure 31:
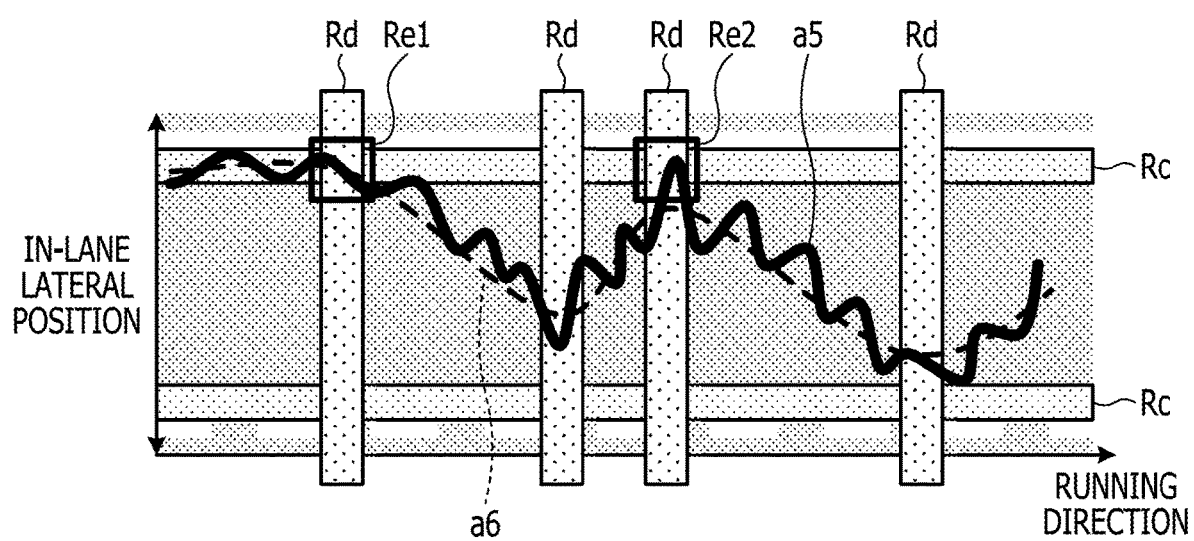
FIG. 31 is a diagram for explaining an abrupt steering determination.

The steering evaluator 251 calculates the score value by adding up the values obtained by the filtering processes, and thereby determines whether the steering is an abrupt steering. The adding up of the characteristic amounts obtained by the filtering processes provides a high evaluation value when all the values obtained by the filtering process are high. FIG. 31 is a diagram for explaining an abrupt steering determination.

A reference sign a5 in FIG. 31 denotes a high-frequency component of the running trace, while a reference sign a6 in FIG. 31 denotes a low-frequency component of the running trace. A value obtained by filtering the lateral displacement amount is high in an area Rc in FIG. 31, while a value obtained by filtering the phase of the in-lane swing is high in an area Rd in FIG. 31. For this reason, a result of evaluating the abrupt steering correction appears more clearly in two areas Re1, Re2 in FIG. 31. In this case, it is determined that the area Re2 is timing with a higher danger level than the area Re1 since the high-frequency power is higher in the area Re2 than in the area Re1.

The steering evaluator 251 obtains the phase of the in-lane swing from the running trace, and thereby identifies four phase ends (Rd). Thereafter, from the four identified phase ends, the steering evaluation 251 extracts the points Re1, Re2 where the vehicle becomes located close to the white line based on the in-lane lateral position (a5). Subsequently, from the points Re1, Re2, the steering evaluator 251 identifies the point Re2 where the short-cycle abrupt steering power is larger than the threshold. Thus, the steering evaluator 251 evaluates that a dangerous driving occurs at the point Re2 in the running trace. As discussed above, from the phase of the in-lane swing and the lateral position in the roadway, the steering evaluator 251 narrows down the steering correction timing for avoiding the deviation, and evaluates the abruptness of the steering correction resulting from a decline in the wariness concentration.

The swing evaluator 252 illustrated in FIG. 25 may be configured to evaluate the swing of the driver using the waveform power of the long-cycle vibration component and the waveform power of the intermediate-cycle vibration component. For example, the swing evaluator 252 calculates the score value representing the danger level by adding up the waveform power of the in-lane swing and the waveform power of the normal steering.

Figure 32:
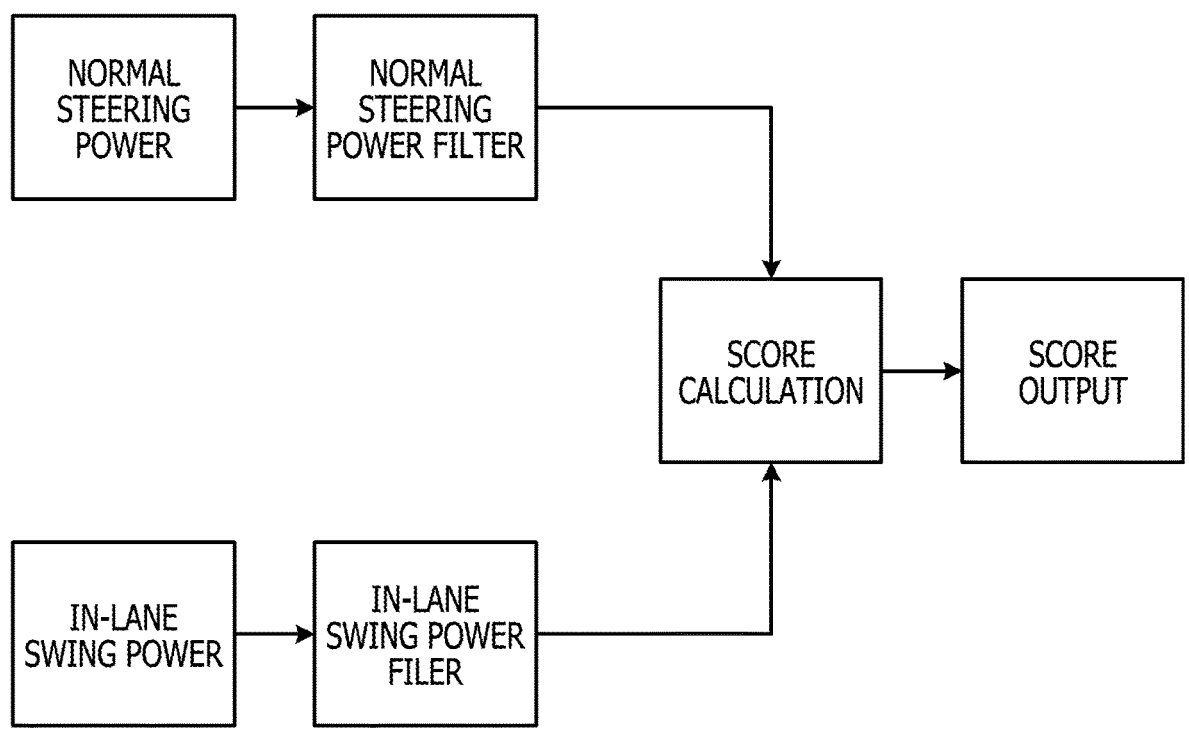
FIG. 32 is a diagram for explaining a process to be performed by a swing evaluator.

FIG. 32 is a diagram for explaining a process to be performed by the swing evaluator 252. As illustrated in FIG. 32, the swing evaluator 252 filters the waveform power of the in-lane swing to normalize the waveform power. Similarly, the swing evaluator 252 filters the waveform power of the normal steering to normalize the waveform power. Thereafter, the swing evaluator 252 calculates the score value by adding up the waveform powers obtained by the filtering process, and outputs the score value to the danger level evaluator 253. Thereby, the swing evaluator 252 performs a control such that the score value is high when the two waveform powers are high, while avoiding a case where the score value is high when either of the two waveform powers is high.

Figure 33:
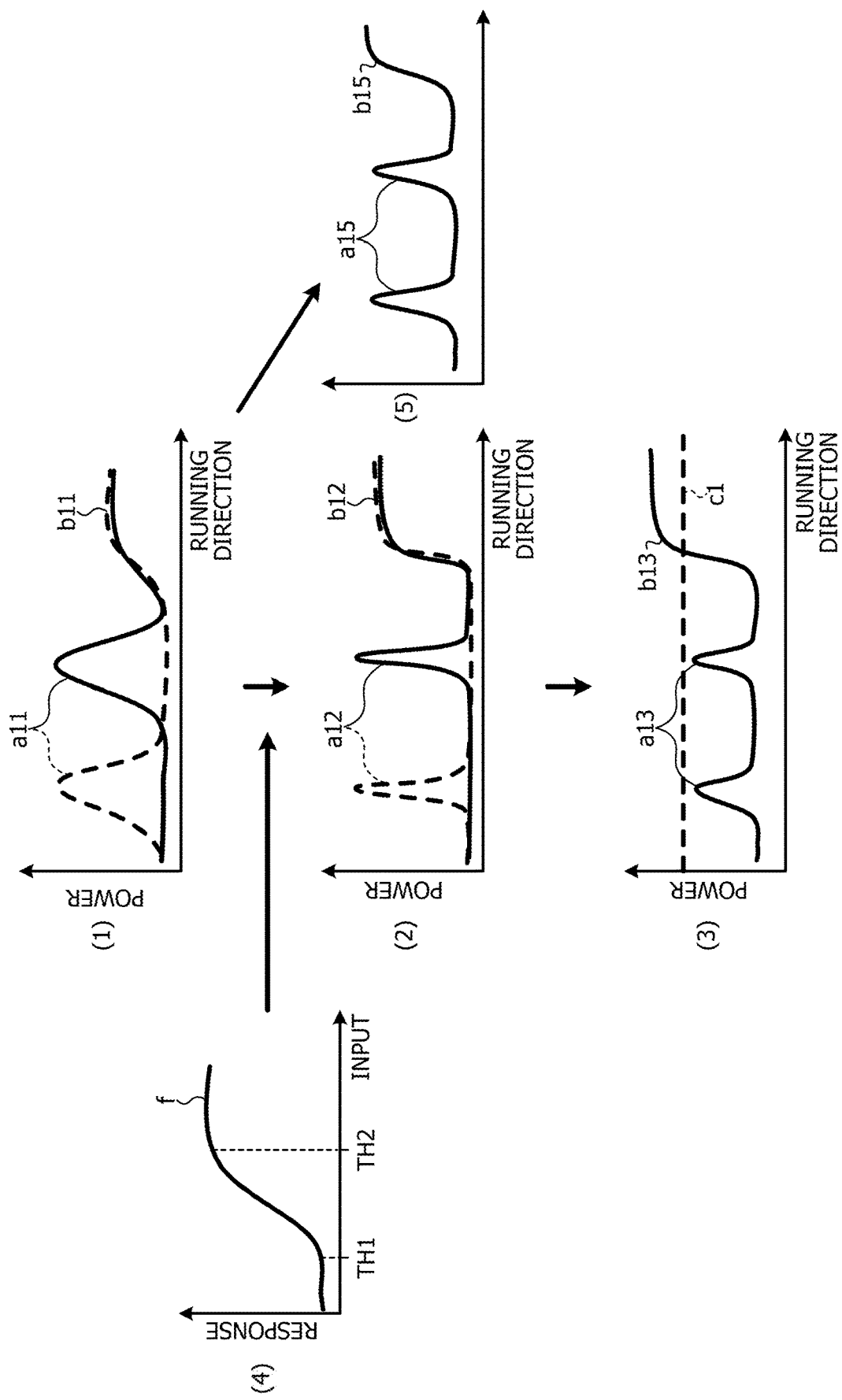
FIG. 33 is a diagram for explaining how to evaluate an overall swing.

FIG. 33 is a diagram for explaining how to evaluate an overall swing. FIG. 33 illustrates both a time-series change in the waveform power of the in-lane swing and a time-series change in the waveform power of the normal steering. Part (1) of FIG. 33 illustrates both the waveform of the in-lane swing and the waveform of the normal steering. Reference sign a11 denotes a state where only one waveform power is high, while reference sign b11 denotes a state where the two waveform powers are high.

Part (5) of FIG. 33 illustrates a case obtained by simply adding up two such waveform powers. In Part (5) pf FIG. 33, the score value in a state a15 where only one waveform power is higher is similar to the score value in a state b15 where the two waveform powers are high. As learned from Part (5) of FIG. 33, it is difficult to determine whether the two powers are high. In a case where the driver is unusual, such a process determines that the steering of the driver is dangerous even though the steering is normal. The process, therefore, fails to identify an intentional abrupt steering different from the normal steering, that is to say, a really dangerous situation.

In contrast to which, the swing evaluator 252 applies a filter illustrated in Part (4) in FIG. 33 to the two waveforms illustrated in Part (1) of FIG. 33. This filter has the same basic characteristics, although a parameter for the normal steering is different from a parameter for the in-lane swing. For example, this filter has the characteristics in which: a value close to the minimum value is returned in a range up to the a low power threshold TH1; a value close to the maximum value is returned in a range beyond a high power threshold TH2; and a value is returned depending on how large the power is in a range between the thresholds TH1, TH2.

When the swing evaluator 252 subjects the waveforms illustrated in Part (1) of FIG. 33 to a filtering process using the filter illustrated in Part (4) of FIG. 33, the response values of the two powers in the state (b11) where the two waveform powers are high becomes higher (b12). Thereafter, the swing evaluator 252 simply adds up the two powers obtained by the filtering process, and thereby obtains a waveform illustrated in Part (3) of FIG. 33. For example, a power ratio may be used as a weight coefficient depending on the necessity. In Part (3) of FIG. 33, b12 raised in Part (2) of FIG. 33 has a score higher than a region a13 as a result of the adding up, and the score is greater than a predetermined danger level reference c1.

As discussed above, the evaluation of the waveform powers obtained by the filtering process using the filter illustrated in Part (4) of FIG. 33 makes it possible to evaluate the state where the two waveform powers of the normal steering and the in-lane swing increase, in addition to the amplitudes of the two waveform powers. This makes it possible to robustly and continuously identify the state where the wariness concentration declines. When the response value of each filter is set within the same range of, for example, 0 to 1.0, it is possible to normalize and thereby evaluate increases in the different power ranges.

The danger level evaluator 253 illustrated in FIG. 25 may be configured to calculate an evaluation value by adding up the score value calculated by the steering evaluator 251 and the score value calculated by the swing evaluator 252.

The swing evaluation may be performed before the steering evaluation, or vice versa. The order of the processes may be changed arbitrarily. Only one of the swing evaluation and the steering evaluation may be performed. Otherwise, both evaluations may be performed.

(Numerical Values)

The numerical values and the thresholds discussed in the foregoing embodiments are merely examples, and are not limited to the specific values mentioned therein.

(Methods)

Although the foregoing embodiments have discussed the hybrid waveform estimation obtained by combing the method A and the method B, the waveform estimation is not limited to the hybrid waveform estimation. For example, the swing waveform estimation may be performed using one of the two methods, such as using the method B alone.

(System)

The processors illustrated in FIG. 5 are not necessarily configured physically as illustrated in FIG. 5. For example, the processors may be configured by dispersion or integration on a unit-to-unit basis. For example, the first to third waveform estimators 22 to 24 may be integrated into a single unit. All or arbitrary parts of the process functions to be performed by the respective processors may be implemented by a central processing unit (CPU) and a program which is analyzed and executed by the CPU, or may be implemented as hardware based on wired logic. The information, inclusive of the process procedures, control procedures, specific names, various data and parameters, discussed in the document or illustrated in the drawings may be arbitrarily changed unless otherwise noted.

(Hardware Configuration)

Figure 34:
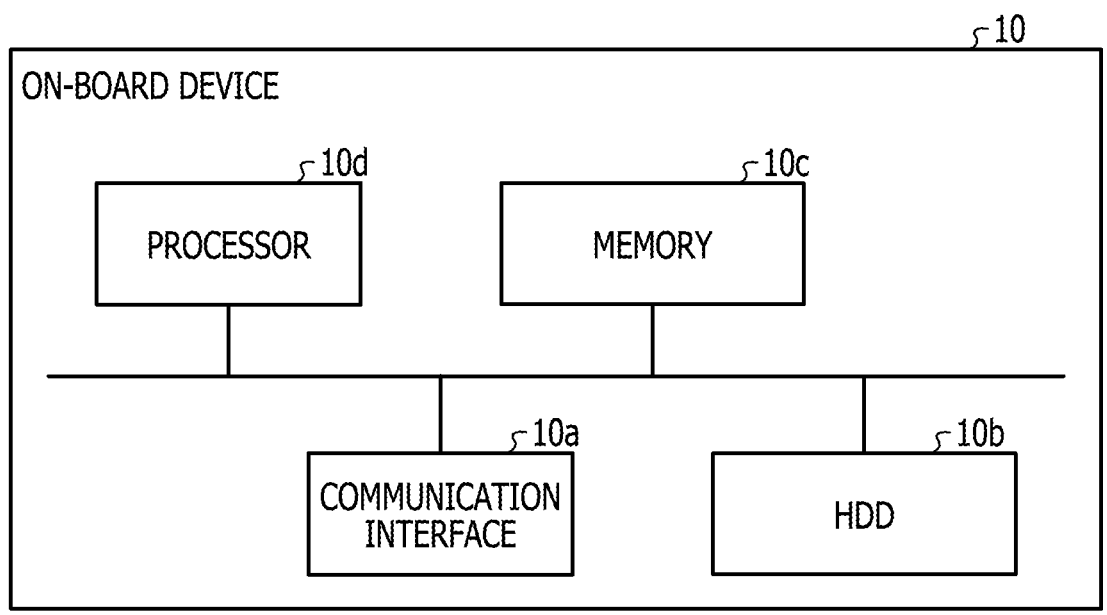
FIG. 34 is a diagram for explaining an example of a hardware configuration.

The on-board device 10 may be implemented, for example, by a computer with the following hardware configuration. FIG. 34 is a diagram illustrating an example of the hardware configuration. As illustrated in FIG. 34, the on-board device 10 includes a communication interface 10a, a hard disk drive (HDD) 10b, a memory 10c, and a processor 10d.

An example of the communication interface 10a is a network interface card. The HDD 10b is a storage which stores the DBs illustrated in FIG. 3 and the like.

Examples of the memory 10c are a random access memory (RAM) such as a synchronous dynamic random access memory (SDRAM), a read-only memory (ROM), and a flash memory. Examples of the processor 10d are a CPU, a digital signal processor (DSP), a field programmable gate array (FPGA), and a programmable logic device (PLD).

The on-board device 10 works as an information processor which performs the waveform estimation method by reading and executing the program. The on-board device 10 executes the program for performing the same functions as the trace generator 21, the first waveform estimator 22, the second waveform estimator 23, the third waveform estimator 24, and the danger determination unit 25. Thus, the on-board device 10 performs the processes for performing the same functions as the trace generator 21, the first waveform estimator 22, the second waveform estimator 23, the third waveform estimator 24, and the danger determination unit 25. The program discussed in the other embodiments is not limited to that which are executed by the on-board device 10. This disclosure is similarly applicable to a case where a different computer or server executes the program, and a case where a different computer and server execute the program in cooperation with each other.

The program may be distributed through a network such as the Internet. The program may be recorded onto a computer-readable recording medium such as a hard disk, a flexible disk (FD), a compact disk read-only memory (CD-ROM), a magneto-optical disk (MO) and a digital versatile disc (DVD). The program may be read from the recoding medium, and be executed by a computer.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A waveform estimation apparatus comprising:
   a memory; and
   a processor coupled to the memory and configured to:
   execute a first estimation process that includes estimating a first vibration component corresponding to a first time period by using an input waveform corresponding to the first time period and the first vibration component corresponding to a second time period, the first time period being a time period from a first time point and having a given time length, the second time period being a time period before the first time period and from a second time point through the first time point and having a time length same as the first time period, the first vibration component being a component less than a first frequency, the input waveform being a waveform based on a running trace of a vehicle which runs along a roadway;
   execute a second estimation process that includes estimating the first vibration component corresponding to the first time period by using the input waveform corresponding to the first time period and the first vibration component corresponding to the second time period and further a second vibration component corresponding to the first time period, wherein the second vibration component is a component equal to or greater than the first frequency and being predicted from the second vibration component corresponding to the second time period;
   execute a calculation process that includes calculating the second vibration component corresponding to the first time period from the input waveform corresponding to the first time period by using the first vibration component estimated by the first estimation process and the first vibration component estimated by the second estimation process;
   execute a determination process that includes determining, by using a characteristic amount of the second vibration component calculated by the calculation process, a danger level indicating how dangerously the vehicle is driven; and
   in response to the danger level being higher than a threshold, change a vehicle drive mode of the vehicle.

2. The waveform estimation apparatus according to claim 1, wherein
   the given time length is a time length corresponding to a half wavelength of the input waveform,
   the second time point of the second time period is a time point going back from the first time point by the half wavelength, and
   an end of the first time period is a time point going forward from the first time point by the half wavelength.

3. The waveform estimation apparatus according to claim 1, wherein
   the processor is further configured to execute a prediction process that includes:
   calculating the second vibration component corresponding to the second time period by subtracting the first vibration component corresponding to the second time period from the input waveform corresponding to the second time period; and
   predicting the second vibration component corresponding to the first time period by using an amplitude and a phase of the second vibration component corresponding to the second time period, and
   the second estimation process is configured to estimate the first vibration component corresponding to the first time period, by using the input waveform corresponding to the first time period and the first vibration component corresponding to the second time period and further the second vibration component predicted by the prediction process.

4. The waveform estimation apparatus according to claim 3, wherein the calculation process is configured to:
   calculate the first vibration component to be used in the calculating of the second vibration component, by adding up the first vibration component estimated by the first estimation process, and the first vibration component estimated by the second estimation process; and
   calculate the second vibration component corresponding to the first time period by subtracting the calculated first vibration component from the input waveform corresponding to the first time period.

5. The waveform estimation apparatus according to claim 1, wherein the determining of the quality index includes determining how dangerously the vehicle is driven based on a characteristic amount of the second vibration component.

6. A method for waveform estimation, the method comprising:
   executing a first estimation process that includes estimating a first vibration component corresponding to a first time period by using an input waveform corresponding to the first time period and the first vibration component corresponding to a second time period, the first time period being a time period from a first time point and having a given time length, the second time period being a time period before the first time period and from a second time point through the first time point and having a time length same as the first time period, the first vibration component being a component less than a first frequency, the input waveform being a waveform based on a running trace of a vehicle which runs along a roadway;

executing a second estimation process that includes estimating the first vibration component corresponding to the first time period by using the input waveform corresponding to the first time period and the first vibration component corresponding to the second time period and further a second vibration component corresponding to the first time period, wherein the second vibration component is a component equal to or greater than the first frequency and being predicted from the second vibration component corresponding to the second time period;

executing a calculation process that includes calculating the second vibration component corresponding to the first time period from the input waveform corresponding to the first time period by using the first vibration component estimated by the first estimation process and the first vibration component estimated by the second estimation process;

executing a determination process that includes determining, by using a characteristic amount of the second vibration component calculated by the calculation process, a danger level indicating how dangerously the vehicle is driven; and in response to the danger level being higher than a threshold, change a vehicle drive mode of the vehicle.

7. The method according to claim 6, wherein the given time length is a time length corresponding to a half wavelength of the input waveform, the second time point of the second time period is a time point going back from the first time point by the half wavelength, and an end of the first time period is a time point going forward from the first time point by the half wavelength.

8. The method according to claim 6, further comprising:

executing a prediction process that includes calculating the second vibration component corresponding to the second time period by subtracting the first vibration component corresponding to the second time period from the input waveform corresponding to the second time period, and predicting the second vibration component corresponding to the first time period by using an amplitude and a phase of the second vibration component corresponding to the second time period, and wherein the second estimation process is configured to estimate the first vibration component corresponding to the first time period, by using the input waveform corresponding to the first time period and the first vibration component corresponding to the second time period and further the second vibration component predicted by the prediction process.

9. The method according to claim 8, wherein the calculation process is configured to:

calculate the first vibration component to be used in the calculating of the second vibration component, by adding up the first vibration component during the second period which is estimated by the first estimation process, and the first vibration component during the second period which is estimated by the second estimation process; and calculate the second vibration component corresponding to the first time period by subtracting the calculated first vibration component from the input waveform corresponding to the first time period.

10. The method according to claim 6, wherein the determining of the quality index includes determining how dangerously the vehicle is driven based on a characteristic amount of the second vibration component.

11. A non-transitory computer-readable storage medium for storing a program that causes a processor to execute a process for waveform estimation, the process comprising:

executing a first estimation process that includes estimating a first vibration component corresponding to a first time period by using an input waveform corresponding to the first time period and the first vibration component corresponding to a second time period, the first time period being a time period from a first time point and having a given time length, the second time period being a time period before the first time period and from a second time point through the first time point and having a time length same as the first time period, the first vibration component being a component less than a first frequency, the input waveform being a waveform based on a running trace of a vehicle which runs along a roadway;

executing a second estimation process that includes estimating the first vibration component corresponding to the first time period by using the input waveform corresponding to the first time period and the first vibration component corresponding to the second time period and further a second vibration component corresponding to the first time period, wherein the second vibration component is a component equal to or greater than the first frequency and being predicted from the second vibration component corresponding to the second time period;

executing a calculation process that includes calculating the second vibration component corresponding to the first time period from the input waveform corresponding to the first time period by using the first vibration component estimated by the first estimation process and the first vibration component estimated by the second estimation process;

executing a determination process that includes determining, by using a characteristic amount of the second vibration component calculated by the calculation process, a danger level indicating how dangerously the vehicle is driven; and in response to the danger level being higher than a threshold, change a vehicle drive mode of the vehicle.

12. The non-transitory computer-readable storage medium according to claim 11, wherein the given time length is a time length corresponding to a half wavelength of the input waveform, the second time point of the second time period is a time point going back from the first time point by the half wavelength, and an end of the first time period is a time point going forward from the first time point by the half wavelength.

13. The non-transitory computer-readable storage medium according to claim 11, further comprising:
   executing a prediction process that includes
      calculating the second vibration component corresponding to the second time period by subtracting the first vibration component corresponding to the second time period from the input waveform corresponding to the second time period, and
      predicting the second vibration component corresponding to the first time period by using an amplitude and a phase of the second vibration component corresponding to the second time period, and
   wherein the second estimation process is configured to estimate the first vibration component corresponding to the first time period, by using the input waveform corresponding to the first time period and the first vibration component corresponding to the second time period and further and the second vibration component predicted by the prediction process.

14. The non-transitory computer-readable storage medium according to claim 13, wherein the calculation process is configured to
   calculate the first vibration component to be used in the calculating of the second vibration component, by adding up the first vibration component during the second period which is estimated by the first estimation process, and the first vibration component during the second period which is estimated by the second estimation process; and
   calculate the second vibration component corresponding to the first time period by subtracting the calculated first vibration component from the input waveform corresponding to the first time period.

15. The non-transitory computer-readable storage medium according to claim 11, wherein the determining of the quality index includes determining how dangerously the vehicle is driven based on a characteristic amount of the second vibration component.

* * * * *